(12) United States Patent
Garidel et al.

(10) Patent No.: US 9,884,020 B2
(45) Date of Patent: Feb. 6, 2018

(54) ANTIBODY FORMULATIONS AND METHODS FOR TREATING AL AMYLOIDOSIS

(71) Applicant: PROTHENA THERAPEUTICS LIMITED, Dublin (IE)

(72) Inventors: Patrick Garidel, Ingelheim am Rhein (DE); Isaac Craig Henderson, San Francisco, CA (US); Pamela Klein, San Mateo, CA (US)

(73) Assignee: PROTHENA THERAPEUTICS LIMITED, Dublin (IE)

( * ) Notice: Subject to any disclaimer, the term of this patent is extended or adjusted under 35 U.S.C. 154(b) by 0 days.

(21) Appl. No.: 15/139,628

(22) Filed: Apr. 27, 2016

(65) Prior Publication Data

US 2016/0310430 A1 Oct. 27, 2016

Related U.S. Application Data

(62) Division of application No. 14/720,505, filed on May 22, 2015, now abandoned, which is a division of application No. 13/660,957, filed on Oct. 25, 2012, now Pat. No. 9,089,529.

(60) Provisional application No. 61/551,406, filed on Oct. 25, 2011.

(51) Int. Cl.
| | |
|---|---|
| A61K 39/395 | (2006.01) |
| A61K 9/19 | (2006.01) |
| A61K 47/26 | (2006.01) |
| C07K 16/18 | (2006.01) |
| A61K 31/198 | (2006.01) |
| A61K 31/454 | (2006.01) |
| A61K 31/69 | (2006.01) |
| A61K 38/07 | (2006.01) |
| A61K 31/195 | (2006.01) |
| A61K 47/22 | (2006.01) |
| A61K 39/00 | (2006.01) |

(52) U.S. Cl.
CPC .............. *A61K 9/19* (2013.01); *A61K 31/195* (2013.01); *A61K 31/198* (2013.01); *A61K 31/454* (2013.01); *A61K 31/69* (2013.01); *A61K 38/07* (2013.01); *A61K 39/3955* (2013.01); *A61K 47/22* (2013.01); *A61K 47/26* (2013.01); *C07K 16/18* (2013.01); *A61K 39/39591* (2013.01); *A61K 2039/505* (2013.01); *A61K 2039/545* (2013.01); *C07K 2317/14* (2013.01); *C07K 2317/24* (2013.01); *C07K 2317/41* (2013.01); *C07K 2317/56* (2013.01); *C07K 2317/565* (2013.01); *C07K 2317/76* (2013.01)

(58) Field of Classification Search
CPC .......... A61K 39/3955; A61K 39/39591; A61K 2039/505; C07K 2317/24; C07K 2317/56
See application file for complete search history.

(56) References Cited

U.S. PATENT DOCUMENTS

| | | |
|---|---|---|
| 5,334,380 A | 8/1994 | Kilbourn et al. |
| 5,348,730 A | 9/1994 | Greenleaf |
| 5,354,562 A | 10/1994 | Platz et al. |
| 5,580,856 A | 12/1996 | Prestrelski et al. |
| 5,589,167 A | 12/1996 | Cleland et al. |
| 5,654,337 A | 8/1997 | Roentsch et al. |
| 5,750,142 A | 5/1998 | Friedman et al. |
| 5,753,219 A | 5/1998 | Cleland et al. |
| 5,804,557 A | 9/1998 | Cleland et al. |
| 5,897,876 A | 4/1999 | Rudnic et al. |
| 5,945,098 A | 8/1999 | Sarno et al. |
| 5,985,320 A | 11/1999 | Edwards et al. |
| 6,165,500 A | 12/2000 | Cevc |
| 6,171,586 B1 | 1/2001 | Lam et al. |
| 6,267,958 B1 | 7/2001 | Andya et al. |
| 6,290,991 B1 | 9/2001 | Roser et al. |
| 6,309,663 B1 | 10/2001 | Patel et al. |
| 6,337,067 B1 | 1/2002 | Yamashita et al. |
| 6,358,530 B1 | 3/2002 | Eljamal et al. |
| 6,465,425 B1 | 10/2002 | Tracy et al. |
| 6,524,557 B1 | 2/2003 | Backstrom et al. |
| 6,565,871 B2 | 5/2003 | Roser et al. |
| 6,579,688 B2 | 6/2003 | Steaffens et al. |
| 6,582,728 B1 | 6/2003 | Platz et al. |
| 6,582,729 B1 | 6/2003 | Eljamal et al. |
| 6,589,560 B2 | 7/2003 | Foster et al. |
| 6,653,062 B1 | 11/2003 | Depablo et al. |
| 6,669,963 B1 | 12/2003 | Kampinga |
| RE38,431 E | 2/2004 | Miekka et al. |
| 6,685,940 B2 | 2/2004 | Andya et al. |
| 6,692,767 B2 | 2/2004 | Burnside et al. |
| 6,794,357 B1 | 9/2004 | Backstrom et al. |
| 6,821,515 B1 | 11/2004 | Cleland et al. |
| 6,841,168 B1 | 1/2005 | Worrall |

(Continued)

FOREIGN PATENT DOCUMENTS

| | | |
|---|---|---|
| EP | 0 229 810 B1 | 10/1991 |
| EP | 0 314 095 B1 | 12/1992 |
| EP | 0 621 774 B1 | 12/1996 |
| EP | 0 315 968 B2 | 4/1997 |
| EP | 0 663 826 B1 | 12/1998 |
| EP | 0 493 437 B2 | 8/1999 |
| EP | 0 580 778 B1 | 8/1999 |
| EP | 0 686 045 B1 | 11/2000 |
| EP | 0 706 383 B1 | 9/2001 |

(Continued)

OTHER PUBLICATIONS

"Amyloidosis" by Drugs.com. Retrieved Feb. 27, 2017, 4 pages.*

(Continued)

*Primary Examiner* — Kimberly A. Ballard
(74) *Attorney, Agent, or Firm* — Womble Bond Dickinson (US) LLP

(57) ABSTRACT

Antibody formulations and methods useful for prophylaxis or treatment of amyloidosis, including AA amyloidosis and AL amyloidosis.

23 Claims, 6 Drawing Sheets

(56) References Cited

U.S. PATENT DOCUMENTS

| | | |
|---|---|---|
| 6,875,432 B2 | 4/2005 | Liu et al. |
| 6,913,745 B1 | 7/2005 | Schenk |
| 6,919,172 B2 | 7/2005 | Depablo et al. |
| 6,991,790 B1 | 1/2006 | Lam et al. |
| 7,060,268 B2 | 6/2006 | Andya et al. |
| 7,132,100 B2 | 11/2006 | Oliver et al. |
| 7,135,180 B2 | 11/2006 | Truong-Le et al. |
| 7,138,141 B2 | 11/2006 | Platz et al. |
| 7,141,236 B2 | 11/2006 | Bot et al. |
| 7,258,869 B1 | 8/2007 | Berry et al. |
| 7,258,873 B2 | 8/2007 | Truong-Le et al. |
| 7,294,336 B2 | 11/2007 | Oliver et al. |
| 7,318,931 B2 | 1/2008 | Okumu et al. |
| 7,364,736 B2 | 4/2008 | Boyle et al. |
| 7,365,166 B2 | 4/2008 | Baca et al. |
| 7,375,193 B2 | 5/2008 | Baca et al. |
| 7,378,110 B2 | 5/2008 | Truong-Le et al. |
| 7,390,786 B2 | 6/2008 | Warne et al. |
| 7,425,618 B2 | 9/2008 | Oliver et al. |
| 7,449,444 B2 | 11/2008 | Warne et al. |
| 7,592,004 B2 | 9/2009 | Kaisheva et al. |
| 7,619,069 B2 | 11/2009 | Davies et al. |
| 7,635,473 B2 | 12/2009 | Warne et al. |
| 7,662,384 B2 | 2/2010 | Ramakrishnan et al. |
| 7,682,609 B2 | 3/2010 | Andya et al. |
| 7,691,379 B2 | 4/2010 | Allan |
| 7,700,130 B2 | 4/2010 | Truong-Le et al. |
| 7,700,739 B2 | 4/2010 | Lacy et al. |
| 7,705,132 B2 | 4/2010 | Rehder et al. |
| 7,740,842 B2 | 6/2010 | Arvinte et al. |
| 7,758,860 B2 | 7/2010 | Warne et al. |
| 7,780,963 B2 | 8/2010 | Acton et al. |
| 7,780,991 B2 | 8/2010 | Roser et al. |
| 7,785,592 B2 | 8/2010 | Oliver et al. |
| 7,785,595 B2 | 8/2010 | Dagan et al. |
| 7,785,631 B2 | 8/2010 | Roser et al. |
| 7,799,900 B2 | 9/2010 | Adams et al. |
| 7,829,525 B2 | 11/2010 | Frevert |
| RE42,012 E | 12/2010 | Deaver et al. |
| 7,883,664 B2 | 2/2011 | Elliott et al. |
| 7,906,109 B2 | 3/2011 | Menart et al. |
| 7,906,119 B1 | 3/2011 | Rosen et al. |
| 7,910,086 B1 | 3/2011 | Sung et al. |
| 7,919,072 B1 | 4/2011 | Sung et al. |
| 7,919,113 B2 | 4/2011 | Domb |
| 7,919,293 B2 | 4/2011 | Sung et al. |
| 7,927,622 B1 | 4/2011 | Cevc et al. |
| 7,927,858 B2 | 4/2011 | Mayeresse |
| 7,928,203 B2 | 4/2011 | Schenk et al. |
| 7,956,160 B2 | 6/2011 | Krishnan |
| 7,959,922 B2 | 6/2011 | Bakker et al. |
| 7,993,624 B2 | 8/2011 | Sung et al. |
| 7,993,625 B1 | 8/2011 | Sung et al. |
| 7,998,458 B2 | 8/2011 | Sung et al. |
| 8,012,485 B2 | 9/2011 | Amphlett et al. |
| 8,025,878 B2 | 9/2011 | Gellerfors et al. |
| 8,025,900 B2 | 9/2011 | Choi et al. |
| 8,043,631 B2 | 10/2011 | Au et al. |
| 8,048,438 B2 | 11/2011 | Berry et al. |
| 8,067,020 B2 | 11/2011 | Okumu et al. |
| 8,067,547 B2 | 11/2011 | Ewert et al. |
| 8,071,537 B2 | 12/2011 | Kuzma et al. |
| 8,084,053 B2 | 12/2011 | Buch-Rasmussen et al. |
| 8,114,380 B2 | 2/2012 | Sung et al. |
| 8,119,604 B2 | 2/2012 | Gombotz et al. |
| 8,142,776 B2 | 3/2012 | Liu et al. |
| 8,173,411 B2 | 5/2012 | Mayeresse |
| 8,188,234 B2 | 5/2012 | Condra et al. |
| 8,206,951 B2 | 6/2012 | Oliver et al. |
| 8,216,583 B2 | 7/2012 | Kruase et al. |
| 8,226,611 B2 | 7/2012 | Chen et al. |
| 8,226,982 B2 | 7/2012 | Schultz-Fademrecht et al. |
| 8,241,632 B2 | 8/2012 | Rehder et al. |
| 8,263,748 B2 | 9/2012 | Li et al. |
| 8,268,354 B2 | 9/2012 | Truong-Le et al. |
| 8,268,973 B2 | 9/2012 | Schenk et al. |
| 8,273,374 B2 | 9/2012 | Truong-Le et al. |
| 8,404,815 B2 | 3/2013 | Schenk et al. |
| 2004/0197324 A1 | 10/2004 | Liu et al. |
| 2009/0093002 A1 | 4/2009 | Pfeifer et al. |
| 2009/0202432 A1 | 8/2009 | Schenk et al. |
| 2009/0252724 A1 | 10/2009 | Loetscher et al. |
| 2011/0038790 A1 | 2/2011 | Schenk et al. |
| 2011/0070225 A1 | 3/2011 | Goldbach et al. |

FOREIGN PATENT DOCUMENTS

| | | |
|---|---|---|
| EP | 0 626 850 B1 | 5/2002 |
| EP | 0 797 431 B1 | 5/2002 |
| EP | 0 999 853 B1 | 1/2003 |
| EP | 1 131 059 B1 | 3/2003 |
| EP | 0 762 897 B1 | 4/2003 |
| EP | 0 831 790 B1 | 5/2003 |
| EP | 0 914 166 B1 | 7/2003 |
| EP | 0 941 067 B1 | 7/2003 |
| EP | 1 173 151 B1 | 7/2003 |
| EP | 0 820 521 B1 | 9/2003 |
| EP | 0 773 781 B1 | 10/2003 |
| EP | 0 825 885 B1 | 3/2004 |
| EP | 0 941 121 B1 | 9/2004 |
| EP | 1 173 245 B1 | 9/2004 |
| EP | 1 187 907 B1 | 9/2004 |
| EP | 1 028 712 B1 | 1/2005 |
| EP | 1 242 576 B1 | 4/2005 |
| EP | 1 117 383 B1 | 11/2005 |
| EP | 1 176 981 B1 | 11/2005 |
| EP | 0 736 041 B1 | 2/2006 |
| EP | 1 152 749 B1 | 4/2006 |
| EP | 1 007 000 B1 | 5/2006 |
| EP | 1 303 184 B1 | 9/2006 |
| EP | 1 729 794 B1 | 7/2008 |
| EP | 1 455 824 B1 | 8/2008 |
| EP | 1 018 345 B1 | 12/2008 |
| EP | 1 809 237 B1 | 12/2008 |
| EP | 1 324 776 B1 | 9/2009 |
| EP | 1 682 180 B1 | 11/2009 |
| EP | 1 409 018 B1 | 1/2010 |
| EP | 1 687 031 B1 | 2/2010 |
| EP | 1 572 744 B1 | 6/2010 |
| EP | 1 531 862 B1 | 8/2010 |
| EP | 1 610 820 B1 | 9/2010 |
| EP | 1 475 101 B1 | 10/2010 |
| EP | 2 004 688 B1 | 12/2010 |
| EP | 1 791 868 B1 | 2/2011 |
| EP | 1 648 485 B1 | 4/2011 |
| EP | 0 996 423 B1 | 6/2011 |
| EP | 1 585 502 B1 | 6/2011 |
| EP | 2 089 008 B1 | 7/2011 |
| EP | 1 755 659 B1 | 11/2011 |
| EP | 1 666 026 B1 | 12/2011 |
| EP | 1 685 152 B1 | 4/2012 |
| EP | 1 441 589 B1 | 5/2012 |
| EP | 1 802 344 B1 | 8/2012 |
| EP | 1 853 310 B1 | 8/2012 |
| EP | 2 238 985 B1 | 8/2012 |
| EP | 2 331 078 B1 | 9/2012 |
| EP | 2 234 600 B1 | 8/2014 |
| EP | 2 328 559 B1 | 1/2015 |
| WO | WO 2004/091658 | 10/2004 |
| WO | WO 2007/068429 | 6/2007 |
| WO | WO 2008/071394 | 6/2008 |
| WO | WO 2009/086539 | 7/2009 |
| WO | WO 2010059787 A1 * | 5/2010 ........... A61K 9/0019 |

OTHER PUBLICATIONS

Hrncic R et al. Antibody-mediated resolution of light chain-associated amyloid deposits. Am. J. Pathol. 2000, 157(4):1239-1246.*

"Multiple Myeloma Prevention", from Multiple Myeloma Research Foundation (MMRF) website retrieved Feb. 27, 2017 from www.themmrf.org.*

(56) References Cited

OTHER PUBLICATIONS

Reece DE et al. Weekly and twice-weekly bortezomib in patients with systemic AL amyloidosis: results of a phate 1 dose-escalatioin study. Blood, 2009, 114(8):1489-1497.*
Renz M et al. 2A4 binds soluble and insoluble light chain aggregates from AL amyloidosis patients and promotes clearance of amyloid deposits by phagocytosis. Amyloid, 2016, 23(3):168-177.*
Declaration of Jun Liu pursuant to 37 C.F.R. 1.132, filed in the prosecution of U.S. Appl. No. 10/813,483 on Sep. 4, 2008.*
Official action dated Jul. 20, 2016, issued in Chinese application (No. 201280052471.6).
Official action dated Jun. 17, 2016, issued in Japanese application (No. 2014-539007).
Official action dated Nov. 11, 2016, issued in Australian application (No. 2012328739).
Official action dated Oct. 4, 2016, issued in Chilean application (No. 01081-2014).
Official action dated Jan. 15, 2017, issued in Israeli application (No. 232213).
Bhambhani et al., "Lyophilization Strategies for Development of a High-Concentration Monoclonal Antibody Formulation: Benefits and Pitfalls," *American Pharmaceutical Review*, 2010, 13(1): 1-9.
Carpenter et al., "Rational Design of Stable Lyophilized Protein Formulations: Theory and Practice," *Pharm Biotechnol.*, 2002,13: 109-33.
Jameel, F. and Hershenson, S., editors, "Formulation and Process Development Strategies for Manufacturing Biopharmaceuticals," Wiley, 2010, pp. 149-151.
Rudikoff et al., "Single amino acid substitution altering antigen-binding specificity," *Proc. Natl. Acad. Sci.*, 1982, 79: 1797-1983.
Wall et al., "Generation and characterization of anti-AA amyloid-specific monoclonal antibodies," *Frontiers in Immunology*, 2011, vol. 2, Article 32, pp. 1-11.
Warne, "Development of high concentration protein biopharmaceuticals: The use of platform approaches in formulation development," *European Journal of Pharmaceutics and Biopharmaceutics*, 2011, 78: 208-212.
Warne et al., "Formulation development of phase 1-2 Biopharmaceuticals: An Efficient and Timely Approach," *Formulation and Process Development Strategies for Manufacturing Biopharmaceuticals*, 2010, Chapter 6, pp. 147-159; Edited by Jameel & Hershenson.
Official action dated Apr. 1, 2016, issued in Canadian application (No. 2,853,112).
Official Action dated Mar. 16, 2015, issued in Chinese application (No. 201280052471.6).
Official action dated Nov. 27, 2015, issued in Chinese application (No. 201280052471.6).
Official action issued in Colombian application (No. 14-088.662).
Official Action dated Feb. 20, 2015, issued in New Zealand application (No. 623606).
International Search Report dated Mar. 15, 2013, issued in International application (No. PCT/US2012/061950).
Written Opinion dated Mar. 15, 2013, issued in International application (No. PCT/US2012/061950).
International Preliminary Report on Patentability (IPRP) dated Apr. 29, 2014, in International application (No. PCT/US2012/061950).
Search report dated Jun. 3, 2015, issued in EP application (No. 12843242.4).
Official action dated Oct. 3, 2014, issued in U.S. Appl. No. 13/660,957.
Official action dated Aug. 29, 2016, issued in Eurasian application (No. 201490850).
Official action dated Feb. 16, 2017, issued in Japanese application (No. 2014-539007).
Official action dated Mar. 28, 2017, issued in Canadian application (No. 2853112).
Official action dated Apr. 5, 2017, issued in Chilean application (No. 2014-001081).
Official action dated Jun. 9, 2017, issued in European application (No. 12843242.4).
Official action dated Jul. 12, 2017, issued in Eurasian application (No. 201490850).
Official action dated Aug. 3, 2017, issued in Japanese application (No. 2016-243114).
Official action dated Sep. 19, 2017, issued in Colombian application (No. 14-088.662).
Official aciton dated Oct. 6, 2017, issued in Mexican application (No. MX/a/2014/004786).

* cited by examiner

FIG. 1A

Humanized 2A4 IgG1 Heavy Chain Variant 2 (G1m3 allotype):

```
     EVQLVESGGG LVQPGGSLRL SCAASGFTFN TYAMYWIRQA PGKGLEWVAR
 51  IRSKSNNYAI YYADSVKDRF TISRDDSKNS LYLQMNSLKT EDTAVYYCAR
101  PYSDSFAYWG QGTLVTVSSA STKGPSVFPL APSSKSTSGG TAALGCLVKD
151  YFPEPVTVSW NSGALTSGVH TFPAVLQSSG LYSLSSVVTV PSSSLGTQTY
201  ICNVNHKPSN TKVDKRVEPK SCDKTHTCPP CPAPELLGGP SVFLFPPKPK
251  DTLMISRTPE VTCVVVDVSH EDPEVKFNWY VDGVEVHNAK TKPREEQYNS
301  TYRVVSVLTV LHQDWLNGKE YKCKVSNKAL PAPIEKTISK AKGQPREPQV
351  YTLPPSREEM TKNQVSLTCL VKGFYPSDIA VEWESNGQPE NNYKTTPPVL
401  DSDGSFFLYS KLTVDKSRWQ QGNVFSCSVM HEALHNHYTQ KSLSLSPGK
(SEQ ID NO: 15)
```

Humanized 2A4 Kappa Light Chain:

```
     DVVMTQSPLS LPVTPGEPAS ISCRSSQSLV HSTGNTYLHW YLQKPGQSPQ
 51  LLIYKVSNRF SGVPDRFSGS GSGTDFTLKI SRVEAEDVGV YYCSQSTHVP
101  FTFGGGTKVE IKRTVAAPSV FIFPPSDEQL KSGTASVVCL LNNFYPREAK
151  VQWKVDNALQ SGNSQESVTE QDSKDSTYSL SSTLTLSKAD YEKHKVYACE
201  VTHQGLSSPV TKSFNRGEC
(SEQ ID NO: 13)
```

FIG. 1B

Humanized 2A4 IgG1 heavy chain variant 1 (G1m1 allotype)

```
  1 EVQLVESGGG LVQPGGSLRL SCAASGFTFN TYAMYWIRQA PGKGLEWVAR
 51 IRSKSNNYAI YYADSVKDRF TISRDDSKNS LYLQMNSLKT EDTAVYYCAR
101 PYSDSFAYWG QGTLVTVSSA STKGPSVFPL APSSKSTSGG TAALGCLVKD
151 YFPEPVTVSW NSGALTSGVH TFPAVLQSSG LYSLSSVVTV PSSSLGTQTY
201 ICNVNHKPSN TKVDKRVEPK SCDKTHTCPP CPAPELLGGP SVFLFPPKPK
251 DTLMISRTPE VTCVVVDVSH EDPEVKFNWY VDGVEVHNAK TKPREEQYNS
301 TYRVVSVLTV LHQDWLNGKE YKCKVSNKAL PAPIEKTISK AKGQPREPQV
351 YTLPPSRDEL TKNQVSLTCL VKGFYPSDIA VEWESNGQPE NNYKTTPPVL
401 DSDGSFFLYS KLTVDKSRWQ QGNVFSCSVM HEALHNHYTQ KSLSLSPGK
(SEQ ID NO: 14)
```

Humanized 2A4 IgG2 heavy chain

```
  1 EVQLVESGGG LVQPGGSLRL SCAASGFTFN TYAMYWIRQA PGKGLEWVAR
 51 IRSKSNNYAI YYADSVKDRF TISRDDSKNS LYLQMNSLKT EDTAVYYCAR
101 PYSDSFAYWG QGTLVTVSSA STKGPSVFPL APCSRSTSES TAALGCLVKD
151 YFPEPVTVSW NSGALTSGVH TFPAVLQSSG LYSLSSVVTV PSSNFGTQTY
201 TCNVDHKPSN TKVDKTVERK CCVECPPCPA PPVAGPSVFL FPPKPKDTLM
251 ISRTPEVTCV VVDVSHEDPE VQFNWYVDGV EVHNAKTKPR EEQFNSTFRV
301 VSVLTVVHQD WLNGKEYKCK VSNKGLPAPI EKTISKTKGQ PREPQVYTLP
351 PSREEMTKNQ VSLTCLVKGF YPSDIAVEWE SNGQPENNYK TTPPMLDSDG
401 SFFLYSKLTV DKSRWQQGNV FSCSVMHEAL HNHYTQKSLS LSPGK
(SEQ ID NO: 16)
```

FIG. 2

Murine VL 2A4
MKLPVRLLVLMFWIPASSSDVVMTQTPLSLPVSLGDQASISCRSSQSLVHSTGNTYLHWYLQKPGQSPKLLIYKVSNRFSGVPDRFSGS
GSGTYFTLKISRVEAEDLGVYFCSQSTHVPFTFGGGTKLEIK (SEQ ID NO: 1)

Murine VL7D8
MKLPVRLLVLMFWIPASSSDVVMTQTPLSLPVSLGDQASISCRSSLSLVHSTGNTYLHWYLQKPGQSPKLLIYKVSNRFSGVPDRFSGS
GSGTYFTLKISRVEAEDLGVYFCSQSTHVPFTFGGGTKLEIK (SEQ ID NO: 2)

Murine VH (2A4 and 7D8)
MVLGLKWVFFVVFYQGVHCEVQLVESGGRLVQPKGSLKLSCAASGFTFNTYAMYWIRQAPGKGLEWVARIRSKSNNYAIYYADSVKDRF
TIFRDDSQSMLYLQMNNLKTEDTAMYYCVRPYSDSFAYWGQGTLVTVSA (SEQ ID NO: 3)

Hum2A4 VL Version 3
DVVMTQSPLSLPVTPGEPASISCRSSQSLVHSTGNTYLHWYLQKPGQSPQLLIYKVSNRFSGVPDRFSGSGSGTDFTLKISRVEAEDVGVYYCSQSTHVPFTFGGGTKVEIK (SEQ ID NO: 4)

Hum2A4/7D8/8G9 VH Version 3
EVQLVESGGGLVQPGGSLRLSCAASGFTFNTYAMYWiRQAPGKGLEWVaRIRSKSNNYAIYYADSVKDRFTISRDDSKNSLYLQMNSLKTEDTAVYYCARPYSDSFAYWGQGTLVTVSS (SEQ ID NO: 5)

Hu2A4 VH3VL3 hcg1,k cDNA sequence / Heavy Chain

```
ATGGAGTTCGGCCTGAGCTGTTCCTGGCTGTTCCTGGTGGCCATCCTGAAGGGCGTGCAGTGCGAG    60
GTGCAGCTGGTGGTCGAGTCCGGCGGCGGAGTCCGTGGTGCAGCCTGGGCGGCTCCCTGAGACTGTCC  120
TGCGCCGCCTCCGGCTTCACCTTCAGCGCCATGTACTGGATCAGGCAGGCTCCT                 180
GGCAAGGGACTGGAGTGGGTGGCCCGGATCAGTGCCAAGTCCAACAACTACGCTATCTAC           240
TACGCCGACTCCGTGAAGGACCGGTTCACCATCTCCCGGGACGACTCCAAGAACTCCCTG           300
TATCTGCAGATGAACTCCCTGCGAAAACCGAGGACACCGCCGTGTACTACTGCGCTCGGCCT         360
TACTCCGACTCCTTCGCTACTGGGGCCAGGCACCCTCGGGGCACCTCTCCCTGTCGACCGTGTCCAGCGCCTCC 420
ACCAAGGGCCCATCGGTCTTCCCCCTGGCACCCTCCCTCCCAAGAGCACCTCTGGGGCACA          480
GCGGCCCTGGGCTGCCTGGTCAAGGACTACTTCCCCGAACCGGTGACGGTGTCGTGGAAC           540
TCAGGCGCCCTGACCAGCGGCGTGCACACCTTCCCGGCTGTCCTACAGTCCTCAGGACTC           600
TACTCCCTCAGCAGCGTGGTGACCGTGCCCTCCAGCAGCTTGGGCACCCAGACCTACATC           660
TGCAACGTGAATCACAAGCCCAGCAACACCAAGGTGGACAAGAGAGTTGAGCCCAAATCT           720
TGTGACAAAACTCACACATGCCCCCCGTGCCCAGCACACCTCATGATCTCCCGGACCCGTCA         780
GTCTTCCTCTTCCCCCCAAAACCCAAGGACACCCTCATGATCTCCCGGACCCCTGAGGTC           840
ACATGCGTGGTGGTGGACGTGAGCCACGAAGACCCTGAGGTCAAGTTCAACTGGTACGTG           900
GACGGCGTGGAGGTGCATAATGCCAAGACAAAGCCGCGGGAGGAGCAGTACAACAGCACG           960
TACCGTGTGGTCAGCGTCCTCACCGTCCTGCACCAGGACTGGCTGAATGGCAAGGAGTAC          1020
AAGTGCAAGGTCTCCAACAAAGCCCTCCCAGCCCCCATCGAGAAAACCATCTCCAAAGCC          1080
AAAGGGCAGCCCCGAGAACCACAGGTGTACACCCTGCCCCCATCCCGGGAGGAGATGACC         1140
AAGAACCAGGTCAGCCTGACCTGCCTGGTCAAAGGCTTCTATCCCAGCGACATCGCCGTG         1200
GAGTGGGAGAGCAATGGGCAGCCGGAGAACAACTACAAGACCACGCCTCCCGTGCTGGAC         1260
TCCGACGGCTCCTTCTTCCTCTATAGCAAGCTCACCGTGGACAAGAGCAGGTGGCAGCAG         1320
GGGAACGTCTTCTCATGCTCCGTGATGCATGAGGCTCTGCACAACCACTACACGCAGAAG         1380
AGCCTCTCCCTGTCCCCGGGTAAATGA                                          1407
```

(SEQ ID NO: 23)

FIG. 4B

Hu2A4 VH3VL3 hcg1,k cDNA sequence / Light Chain

```
ATGGACATGCGGGTGCCCGCACAGCTGCTGGGCCTGCTGATGCTGTGGGTGTCCGGCTCC    60
TCCGGCGACGTGGTGATGACCCAGTCCCCTCTGTCCCTGCCCGTGACCCCTGGCGAGCCT   120
GCCTCCATCTCCTGCCGGTCCTCCCAGTCCCTGCTCCACTCCAACGGCAACACCTATCTG   180
CACTGGTATCTGCAGAAGCCTGGCCAGTCTCCTCAGCTCCTGATCTACAAGGTGTCCAAC   240
CGGTTCTCCGGCGTGCCTGACCGGTTCTCTGGCTCCGGCTCTGGCACCGACTTCACCCTG   300
AAGATCTCCCGGGTGGAGGCCGAGGACGTGGGCGTGTACTACTGCTCCCAGTCCACCCAC   360
GTGCCCTTTCACCTTCGGCGGAGGCACCAAGGTGGAGATCAAGCGAACTGTGGCTGCACCA   420
TCTGTCTTCATCTTCCCGCCATCTGATGAGCAGTTGAAATCTGGAACTGCCTCTGTTGTG   480
TGCCTGCTGAATAACTTCTATCCCAGAGAGGCCAAAGTACAGTGGAAGGTGGATAACGCC   540
CTCCAATCGGGTAACTCCCAGGAGAGTGTCACAGAGCAGGACAGCAAGGACAGCACCTAC   600
AGCCTCAGCAGCACCCTGACGCTGAGCAAAGCAGACTACGAGAAACACAAAGTCTACGCC   660
TGCGAAGTCACCCATCAGGGCCTGAGCTCGCCCGTCACAAAGAGCTTCAACAGGGGAGAG   720
TGTTAG                                                          726
(SEQ ID NO: 20)
```

ANTIBODY FORMULATIONS AND METHODS FOR TREATING AL AMYLOIDOSIS

CROSS-REFERENCE TO RELATED APPLICATIONS

This is a divisional of U.S. patent application Ser. No. 14/720,505, filed 22 May 2015, now abandoned, which is a divisional of U.S. patent application Ser. No. 13/660,957, filed 25 Oct. 2012, now U.S. Pat. No. 9,089,529 issued 28 Jul. 28, 2015, which claims priority to provisional Application No. 61/551,406, filed 25 Oct. 2011, which is incorporated by reference herein in its entirety.

TECHNICAL FIELD

The invention resides in the technical fields of immunology and medicine.

BACKGROUND OF THE INVENTION

Amyloidosis is a general term that describes a number of diseases characterized by the existence of pathological forms of amyloid proteins, often involving extracellular deposition of protein fibrils, which form numerous "amyloid deposits" or "amyloid plaques," which may occur in local sites or systematically. These deposits or plaques are composed primarily of a naturally occurring soluble protein or peptide, assembled into extensive insoluble deposits 10-100 μm in diameter in a variety of tissue sites. The deposits are composed of generally lateral aggregates of fibrils that are approximately 10-15 nm in diameter. Amyloid fibrils produce a characteristic apple green birefringence in polarized light, when stained with Congo Red dye. Generally, the fibrillar composition of these deposits is an identifying characteristic for the various forms of amyloid disease.

The peptides or proteins forming the plaque deposits are often produced from a larger precursor protein. More specifically, the pathogenesis of amyloid aggregates such as fibril deposits generally involves proteolytic cleavage of an "abnormal" precursor protein into fragments that aggregate into anti-parallel β pleated sheets.

Systemic amyloidoses are a complex group of diseases caused by tissue deposition of misfolded proteins that result in progressive organ damage. The most common type, AL amyloidosis or primary amyloidosis, involves a hematological disorder caused by clonal plasma cells that produce misfolded immunoglobulin light chains. Overproduction of misfolded light chain by plasma cells results in deposits of abnormal AL protein (amyloid), in the tissues and organs of individuals with AL amyloidosis. Clinical features of AL amyloidosis include a constellation of symptoms and organ dysfunction that can include cardiac, renal, and hepatic dysfunction, gastrointestinal involvement, neuropathies and macroglossia. The mechanisms by which amyloidogenic immunoglobulin light chains result in organ dysfunction are not well characterized, however, it is hypothesized that both amyloid deposits and prefibrillar aggregates may contribute to cytotoxic effects on organs observed in patients with AL amyloidosis. AL amyloidosis is a disease entity of its own, although AL amyloidosis can occur concurrently in a small subset (up to 15%) of patients with multiple myeloma.

AL amyloidosis is a rare disorder with an estimated incidence of 8 in 1,000,000 people. Only 1200 to 3200 new cases of AL amyloidosis are reported each year in the United States. Two thirds of patients with AL amyloidosis are male and less than 5% of patients are under 40 years of age. Both the causes and origins of AL amyloidosis remain poorly understood.

Current treatment of patients with AL amyloidosis is aimed at reducing or eliminating the bone marrow disorder, i.e. the plasma cells that are responsible for producing the light chains, thereby limiting or halting the production of amyloid. The most aggressive treatment options include stem cell transplant and high-dose chemotherapy for those patients who can tolerate it. Other treatment regimens include combinations of drugs often used to treat hematological malignancies, such as melphalan, prednisone, dexamethasone and proteosome inhibitors such as bortezomib, in an attempt to reduce light chain production. There are no currently approved treatments for AL amyloidosis that directly target potentially toxic forms of the amyloidogenic proteins.

A different form of systemic amyloidosis, AA amyloidosis or secondary amyloidosis, occurs "secondarily" as a result of other illness, such as chronic inflammatory diseases (for example, rheumatoid arthritis and ankylosing spondylitis) or chronic infections (for example, tuberculosis or osteomyelitis). In secondary amyloidosis, the depositing amyloid protein is amyloid A protein, derived from an acute-phase protein serum amyloid A. The treatment of secondary amyloidosis is directed at treating the underlying illness.

Thus, there is a need for therapies to treat AA amyloidosis and AL amyloidosis, which directly target the pathological amyloid fibrils. The present invention provides pharmaceutical formulations of 2A4 and 7D8 antibodies, and chimeric and humanized versions thereof, which show high affinity binding to both AL and AA amyloids due to a shared immunogenic epitope of the pathological forms of these proteins.

SUMMARY OF THE INVENTION

The present invention provides antibody formulations useful for prophylaxis and treatment of amyloid disease. In one aspect of the invention, a pharmaceutical formulation comprises (a) a chimeric or humanized version of antibody 2A4 (ATCC Accession Number PTA-9662) or of antibody 7D8 (ATCC Accession Number PTA-9468), or fragment thereof, which specifically competes for binding to antigen with 2A4 or 7D8, and/or which is directed to an epitope comprising AEDS (SEQ ID NO: 18), wherein the antibody is present at a concentration within the range from about 1 mg/mL to about 100 mg/mL; (b) histidine buffer present at a concentration within the range from about 20 mM to about 30 mM; (c) trehalose present at a concentration within the range from about 210 mM to about 250 mM; and (d) polysorbate 20 present at a concentration within the range from about 0.005% to about 0.05% by weight; wherein the formulation is characterized by a pH within the range from about 6 to about 7. For example, representative formulations of the invention comprise an antibody having a light chain variable region comprising an amino acid sequence set forth as SEQ ID NO: 4 and/or a heavy chain variable region comprising an amino acid sequence set forth as SEQ ID NO: 5. More particularly, such a formulation can comprise an antibody having a light chain comprising an amino acid sequence set forth as SEQ ID NO: 13 and a heavy chain comprising an amino acid sequence set forth as any one of SEQ ID NO: 14-16, for example, an antibody having a light chain comprising an amino acid sequence set forth as SEQ ID NO: 13 and a heavy chain comprising an amino acid sequence set forth as SEQ ID NO: 15.

Additional representative formulations of the invention comprise (a) an antibody having a light chain variable region comprising three complementarity determining regions set forth as SEQ ID NOs: 6, 7, and 8, and a heavy chain variable region comprising three complementary regions set forth as SEQ ID NOs: 9, 10, and 11; and (b) an antibody having a light chain variable region comprising three complementarity determining regions set forth as SEQ ID NOs: 12, 7, and 8, and a heavy chain variable region comprising three complementarity regions set forth as SEQ ID NOs: 9, 10, and 11.

In representative formulations of the invention, the antibody is present at a concentration within the range from about 5 mg/mL to about 15 mg/mL (e.g., about 10 mg/mL), or present at a concentration within the range from about 25-75 mg/mL (e.g., 50 mg/mL).

In other representative formulations of the invention, histidine buffer is present at a concentration of about 25 mM. The histidine buffer can comprise L-histidine and L-histidine HCl monohydrate. For example, L-histidine can be used at a concentration within the range from about 16 mM to about 22 mM and L-histidine HCl monohydrate can be used at a concentration within the range from about 4 mM to about 8 mM.

In other representative formulations of the invention, trehalose is present at a concentration of about 230 mM.

Prepared as described herein, representative formulations of the invention (a) are characterized by an osmolality of about 300 mOsm/kg; (b) comprise less than about 10% of the antibody present as an aggregate in the formulation; (c) further comprise a bulking agent; (d) are sterile; and/or (e) are stable upon freezing and thawing.

In one aspect of the invention, a formulation comprises (a) an antibody comprising a light chain comprising an amino acid sequence set forth as SEQ ID NO: 13 and a heavy chain comprising an amino acid sequence set forth as any one of SEQ ID NOs: 14-16, and which is present at a concentration of about 10 mg/mL; (b) a histidine buffer present at a concentration of about 25 mM; (c) trehalose present at a concentration of about 230 mM; (d) polysorbate 20 present at a concentration of about 0.2 g/L; and (e) a pH of about 6.5.

In another aspect of the invention, a pharmaceutical formulation comprises (a) an antibody, which is antibody 2A4 (ATCC Accession Number PTA-9662), antibody 7D8 (ATCC Accession Number PTA-9468), or a chimeric or humanized version of antibody 2A4 or of antibody 7D8, or fragment thereof, which specifically competes for binding to antigen with 2A4 or 7D8, and/or which is directed to an epitope comprising AEDS (SEQ ID NO: 18), wherein the antibody is present at a concentration within the range from about 50 mg/mL to about 100 mg/mL; (b) a buffer; (c) a non-reducing sugar; and (d) a non-ionic surfactant. In particular examples, the antibody of the disclosed formulations comprises a light chain comprising an amino acid sequence set forth as SEQ ID NO: 13 and a heavy chain comprising an amino acid sequence set forth as SEQ ID NOs: 15.

In another aspect of the invention, the antibody formulations are lyophilized. For example, a representative lyophilized formulation can comprise: (a) a humanized version of antibody 2A4 (ATCC Accession Number PTA-9662) or antibody 7D8 (ATCC Accession Number PTA-9468) or antigen binding fragment thereof; (b) histidine; (c) trehalose; and (d) polysorbate 20. Lyophilized formulations can have a pH of between about 6 to about 7 when reconstituted, such as pH 6.5 when reconstituted. Lyophilized formulations typically comprise about 100 mg to about 1000 mg of the antibody. Lyophilized formulations typically comprise polysorbate 20 at a concentration within the range from about 0.005% to about 0.05% by weight. Following reconstitution, the lyophilized formulations yield an aqueous solution, for example, an aqueous solution comprising: (a) an antibody comprising a light chain comprising an amino acid sequence set forth as SEQ ID NO: 13 and a heavy chain comprising an amino acid sequence set forth as any one of SEQ ID NOs: 14-16, and which is present at a concentration of about 10 mg/mL; (b) a histidine buffer present at a concentration of about 25 mM; (c) trehalose present at a concentration of about 230 mM; (d) polysorbate 20 present at a concentration of about 0.2 g/L; and (e) a pH of about 6.5. A representative lyophilized formulation comprises about 100 mg of the antibody following reconstitution with sterile water.

Also provided are nucleic acids encoding antibodies used to prepare the disclosed formulations. For example, such nucleic acids include nucleic acids comprising nucleotide sequences encoding an antibody light chain of SEQ ID NO: 13 and nucleic acids comprising nucleotide sequences encoding an antibody heavy chain of any one of SEQ ID NOs: 14-16. For example, the nucleotide sequences set forth as SEQ ID NO: 19 and SEQ ID NO: 20 (which is identical to SEQ ID NO: 19 and further includes a sequence encoding a signal peptide) each encode the humanized 2A4 light chain of SEQ ID NO: 13. As another example, the nucleotide sequences set forth as SEQ ID NO: 22 and SEQ ID NO: 23 (which is identical to SEQ ID NO: 22 and further includes a sequence encoding a signal peptide) each encode the humanized 2A4 heavy chain of SEQ ID NO: 15.

For the production of antibodies, the disclosed nucleic acids may be included in a vector, either singly or in combination (e.g., a combination of a nucleic acid encoding a humanized 2A4 light chain and a nucleic acid encoding a humanized 2A4 heavy chain). For example, a vector can comprise a nucleic acid comprising a nucleotide sequence encoding any one of SEQ ID NOs: 13-16, 21, and 24; a nucleic acid comprising the nucleotide sequence of any one of SEQ ID NOs: 19-20 and 22-23, or combinations thereof. Representative vectors of the invention include (a) a vector comprising a nucleic acid sequence encoding a humanized 2A4 light chain set forth as SEQ ID NO: 13 or 21 and a humanized 2A heavy chain set forth as SEQ ID NO: 15 or 24; (b) a vector comprising a nucleic acid having the nucleotide sequence of SEQ ID NO: 19 and a nucleic acid having the nucleotide sequence of SEQ ID NO: 22; and (c) a vector comprising a nucleic acid having the nucleotide sequence of SEQ ID NO: 20 and a nucleic acid having the nucleotide sequence of SEQ ID NO: 23.

Also provided are host cells (e.g., CHO cells) having stably incorporated into their genomes one or more of the nucleic acids disclosed herein. For example, a host cell can comprise in its genome a stably integrated nucleic acid comprising a nucleotide sequence encoding any one of SEQ ID NOs: 13-16, 21, and 24; a stably integrated nucleic acid comprising the nucleotide sequence of any one of SEQ ID NOs: 19-20 and 22-23, or combinations thereof. Representative host cells of the invention include (a) host cells comprising a nucleic acid sequence encoding a humanized 2A4 light chain set forth as SEQ ID NO: 13 or 21 and a humanized 2A heavy chain set forth as SEQ ID NO: 15 or 24; (b) host cells comprising a nucleic acid having the nucleotide sequence of SEQ ID NO: 19 and a nucleic acid having the nucleotide sequence of SEQ ID NO: 22; and (c) host cells comprising a nucleic acid having the nucleotide sequence of SEQ ID NO: 20 and a nucleic acid having the nucleotide sequence of SEQ ID NO: 23.

The present invention also provides methods of preparing pharmaceutical formulations. In one aspect of the invention, such a method comprises (a) culturing mammalian cells having stably incorporated into their genome nucleic acids encoding the light and heavy chains of a murine, chimeric or humanized 2A4 antibody or of a murine, chimeric or humanized 7D8 antibody so that the cells secrete the antibody into the cell culture media, and purifying the antibody from the cell culture media; (b) and preparing a formulation comprising (i) a chimeric or humanized version of antibody 2A4 (ATCC Accession Number PTA-9662) or of antibody 7D8 (ATCC Accession Number PTA-9468), or fragment thereof, that specifically competes for binding to antigen with 2A4 or 7D8, wherein the antibody is present at a concentration within the range from about 1 mg/mL to about 100 mg/mL; (ii) histidine buffer present at a concentration within the range from about 20 mM to about 30 mM; (iii) trehalose present at a concentration within the range from about 210 mM to about 250 mM; and (iv) polysorbate 20 present at a concentration within the range from about 0.005% to about 0.05% by weight; wherein the formulation is characterized by a pH within the range from about 6 to about 7. For example, in one aspect of the invention, mammalian cells having stably incorporated into their genomes nucleic acids encoding the light and heavy chains of a humanized 2A4 antibody are cultured. Mammalian cells useful for this purpose include (a) host cells having stably incorporated into their genomes a nucleic acid sequence encoding a humanized 2A4 light chain set forth as SEQ ID NO: 13 or 21 and a humanized 2A heavy chain set forth as SEQ ID NO: 15 or 24; (b) host cells having stably incorporated into their genomes a nucleic acid having the nucleotide sequence of SEQ ID NO: 19 and a nucleic acid having the nucleotide sequence of SEQ ID NO: 22; and (c) host cells having stably incorporated into their genomes a nucleic acid having the nucleotide sequence of SEQ ID NO: 20 and a nucleic acid having the nucleotide sequence of SEQ ID NO: 23. In some aspects of the invention, the disclosed methods of preparing a pharmaceutical formulation include the additional step of evaluating at least one property of antibody in the formulation, such as physical stability, chemical stability, and/or biological activity.

Still further provided are methods of therapeutically or prophylactically treating a human patient having or at risk of having amyloidosis characterized by the presence of amyloid protein fibrils, the method comprising administering to the patient an effective dosage of a formulation of the invention. Patients amenable to treatment have an amyloid disease such as amyloid A amyloidosis, which is characterized by the presence of amyloid A protein fibrils, or AL amyloidosis, which is characterized by the presence of amyloid light chain-type protein fibrils. Patients having AL amyloidosis may also suffer from an associated dyscrasia of the B lymphocyte lineage, for example a malignancy such as multiple myeloma.

The disclosed therapeutic and prophylactic treatment methods include combination therapies (i.e., administration of the disclosed antibody formulations with one or more additional drug substances) to thereby elicit synergistic results. The two or more drug substances are administered simultaneously or sequentially in any order, i.e., a formulation of the invention is administered prior to administration of a second drug substance, concurrently with a second drug substance, or subsequent to administration of a second drug substance. For example, a formulation of the invention can be administered concurrently or consecutively in combination with melphalan. As another example, a formulation of the invention can be administered concurrently or consecutively in combination with one or more of bortezomib, melphalan, lenalidomide and carfilzomib.

In accordance with the disclosed therapeutic and prophylactic treatment methods, formulations of the invention can be administered in multiple dosages, for example, at a frequency in a range of about daily to about annually, such as at a frequency in a range of about every other week to about every three months, or such as once a month. In one aspect, an antibody formulation of the invention is administered intravenously at a dose in a range from about 10 mg to about 5000 mg drug substance. For example, a formulation can be administered at a dose in a range from about 30 mg to about 2500 mg humanized 2A4 drug substance at a frequency in a range of about every other week to about every other month. Representative dosages used in the disclosed methods include 30 mg, 100 mg, 300 mg, 1000 mg, 2000 mg, and 2500 mg of humanized 2A4 drug substance.

In one aspect of the invention, a method of therapeutically or prophylactically treating a human patient having or at risk for having light chain (AL) amyloidosis characterized by the presence of amyloid fibrils, deposits or prefibrillar aggregates, comprises administering to the patient an effective dosage of a pharmaceutical formulation comprising: (a) an antibody comprising a light chain comprising an amino acid sequence set forth as SEQ ID NO: 13 and a heavy chain comprising an amino acid sequence set forth as any one of SEQ ID NOs: 14-16, and which is present at a concentration of about 10 mg/mL; (b) a histidine buffer present at a concentration of about 25 mM; (c) trehalose present at a concentration of about 230 mM; (d) polysorbate 20 present at a concentration of about 0.2 g/L; and (e) a pH of about 6.5. In such a method, the dosage is typically from about 0.5 mg/kg to about 30 mg/kg of the antibody (e.g., about 0.5 mg/kg to about 8 mg/kg, or about 8 mg/kg to about 30 mg/kg) administered intravenously or subcutaneously at a frequency of from about weekly to about quarterly (e.g., once every 28 days).

The present invention further provides a pharmaceutical product comprising: (a) a vial comprising about 100 mg antibody in powder form; (b) instructions for reconstitution of the antibody; and (c) instructions for preparing the reconstituted antibody for infusion, wherein (i) the antibody comprises a light chain comprising an amino acid sequence set forth as SEQ ID NO: 13 and a heavy chain comprising an amino acid sequence set forth as any one of SEQ ID NOs: 14-16; and (ii) the reconstitution instructions require reconstitution with water for injection to an extractable volume of 10 mL.

BRIEF DESCRIPTION OF THE DRAWINGS

FIGS. 1A-1B show various humanized 2A4 antibody light chain and heavy chain sequences. Bold and underlining, consensus sequence for N-linked glycosylation.

FIG. 2 shows murine 2A4 and 7D8 light chain variable region (VL) and heavy chain variable region (VH) sequences. Double underlining, leader sequence; underlining, complementarity determining region (CDR) sequences.

FIG. 3 shows humanized 2A4 version 3 light chain variable region (VL) and heavy chain variable region (VH) sequences. Lower case, back mutations.

FIGS. 4A-4B show nucleic acid sequences encoding humanized 2A4 version 3 heavy chain (FIG. 4A) and heavy chain (FIG. 4B) sequences. Single underline, leader sequence; no underline, variable region; double underline, constant region.

DETAILED DESCRIPTION OF THE INVENTION

The present invention provides antibody formulations useful for prophylaxis and treatment of amyloid disease. In one aspect of the invention, a pharmaceutical formulation comprises (a) a chimeric or humanized version of antibody 2A4 (ATCC Accession Number PTA-9662) or of antibody 7D8 (ATCC Accession Number PTA-9468), or fragment thereof, which specifically competes for binding to antigen with 2A4 or 7D8, and/or which is directed to an epitope comprising AEDS (SEQ ID NO: 18), wherein the antibody is present at a concentration within the range from about 1 mg/mL to about 100 mg/mL; (b) histidine buffer present at a concentration within the range from about 20 mM to about 30 mM; (c) trehalose present at a concentration within the range from about 210 mM to about 250 mM; and (d) polysorbate 20 present at a concentration within the range from about 0.005% to about 0.05% by weight; wherein the formulation is characterized by a pH within the range from about 6 to about 7.

In one aspect of the invention described herein, humanized 2A4 is an IgG1, kappa isotype version of murine 2A4. In the course of specificity characterization of humanized 2A4, the antibody was found to also react with high affinity and in a conformation-dependent manner with light chain in light chain amyloid fibrils, but not with free light chain in circulation.

The present invention provides methods for intravenous infusion of humanized 2A4 and/or humanized 7D8 antibodies to target misfolded amyloid protein in patients with AA amyloidosis and AL amyloidosis. Some humanized 2A4 antibodies specifically bind to pathologic amyloid forms of AL and SAA but do not bind to the parent molecules from which these pathologic forms are derived (SAA, native immunoglobulin light chain [LC], intact immunoglobulin [Ig]).

I. Pharmaceutical Formulations and Products

I.A. Characteristics

Provided herein are pharmaceutical formulations comprising a chimeric or humanized version of antibody 2A4 (ATCC Accession Number PTA-9662) or of antibody 7D8 (ATCC Accession Number PTA-9468), or fragment thereof, that specifically competes for binding to antigen (i.e., human AA or AL protein) with 2A4 or 7D8, respectively, and/or that is directed to the epitope AEDS (SEQ ID NO: 18). Also provided are pharmaceutical formulations comprising murine antibody 2A4 or murine antibody 7D8, or fragments thereof. The antibody is present at a concentration within the range from about 1 mg/mL to about 100 mg/mL. The formulation is characterized by a pH within the range from about 6 to about 7 and comprises a histidine buffer at a concentration within the range from about 20 mM to about 30 mM, trehalose at a concentration within the range from about 210 mM to about 250 mM; and polysorbate 20 at a concentration within the range from about 0.005% to about 0.05% by weight.

The term "humanized immunoglobulin" or "humanized antibody" refers to an immunoglobulin or antibody that includes at least one humanized immunoglobulin or antibody chain (i.e., at least one humanized light or heavy chain). The term "humanized immunoglobulin chain" or "humanized antibody chain" (i.e., a "humanized immunoglobulin light chain" or "humanized immunoglobulin heavy chain") refers to an immunoglobulin or antibody chain (i.e., a light or heavy chain, respectively) having a variable region that includes a variable framework region substantially from a human immunoglobulin or antibody and complementarity determining regions (CDRs) (e.g., at least one CDR, preferably two CDRs, more preferably three CDRs) substantially from a non-human immunoglobulin or antibody, and further includes constant regions (e.g., at least one constant region or portion thereof, in the case of a light chain, and preferably three constant regions in the case of a heavy chain). The term "humanized variable region" (e.g., "humanized light chain variable region" or "humanized heavy chain variable region") refers to a variable region that includes a variable framework region substantially from a human immunoglobulin or antibody and complementarity determining regions (CDRs) substantially from a non-human immunoglobulin or antibody.

The phrase "substantially from a human immunoglobulin or antibody" or "substantially human" means that, when aligned to a human immunoglobulin or antibody amino sequence for comparison purposes, the region shares at least 80-90%, preferably 90-95%, more preferably 95-99% identity (i.e., local sequence identity) with the human framework or constant region sequence, allowing, for example, for conservative substitutions, consensus sequence substitutions, germline substitutions, backmutations, and the like. The introduction of conservative substitutions, consensus sequence substitutions, germline substitutions, backmutations, and the like, is often referred to as "optimization" of a humanized antibody or chain. The phrase "substantially from a non-human immunoglobulin or antibody" or "substantially non-human" means having an immunoglobulin or antibody sequence at least 80-95%, preferably 90-95%, more preferably, 96%, 97%, 98%, or 99% identical to that of a non-human organism, e.g., a non-human mammal.

Accordingly, all regions or residues of a humanized immunoglobulin or antibody, or of a humanized immunoglobulin or antibody chain, except possibly the CDRs, are substantially identical to the corresponding regions or residues of one or more native human immunoglobulin sequences. The term "corresponding region" or "corresponding residue" refers to a region or residue on a second amino acid or nucleotide sequence which occupies the same (i.e., equivalent) position as a region or residue on a first amino acid or nucleotide sequence, when the first and second sequences are optimally aligned for comparison purposes.

In some formulations, the antibody comprises a light chain variable region comprising an amino acid sequence set forth as any one of SEQ ID NOs: 1, 2, or 4. In some formulations, the antibody comprises a heavy chain variable region comprising an amino acid sequence set forth as SEQ ID NO: 3 or 5. In some formulations, the antibody comprises a light chain variable region comprising an amino acid sequence set forth as any one of SEQ ID NOs: 1, 2, or 4 and a heavy chain variable region comprising an amino acid sequence set forth as SEQ ID NO: 3 or 5. In some formulations, the antibody comprises a light chain variable region comprising an amino acid sequence set forth as SEQ ID NO: 1 and a heavy chain variable region comprising an amino acid sequence set forth as SEQ ID NO: 3. In some formulations, the antibody comprises a light chain variable region comprising an amino acid sequence set forth as SEQ ID NO: 4 and a heavy chain variable region comprising an amino acid sequence set forth as SEQ ID NO: 5. In some formulations, the antibody comprises a light chain variable region comprising an amino acid sequence set forth as SEQ ID NO: 2 and a heavy chain variable region comprising an amino acid sequence set forth as SEQ ID NO: 3.

In some formulations, the antibody comprises a light chain variable region comprising three complementarity determining regions set forth as SEQ ID NOs: 6, 7, and 8, and a heavy chain variable region comprising three complementarity regions set forth as SEQ ID NOs: 9, 10, and 11. In other formulations, the antibody comprises a light chain variable region comprising three complementarity determining regions set forth as SEQ ID NOs: 12, 7, and 8, and a heavy chain variable region comprising three complementarity regions set forth as SEQ ID NOs: 9, 10, and 11.

In other formulations of the present invention, the antibody comprises light chain and heavy chain variable regions of a murine, chimeric, or humanized 2A4 antibody, or of a murine, chimeric, or humanized 7D8 antibody, as described in U.S. Pat. No. 7,928,203 and PCT International Publication No. WO 2009/086539, each of which is incorporated herein by reference in its entirety, and the light chain and heavy chain variable region sequences described in the referenced patent and publication are specifically incorporated by reference herein.

In some formulations, the antibody comprises a light chain comprising an amino acid sequence set forth as SEQ ID NO: 13 or 21 and a heavy chain comprising an amino acid sequence set forth as any one of SEQ ID NOs: 14-16 and 24. The antibody can include, or not include, the leader sequences of the above-noted light chain and heavy chain amino acid sequences.

In other formulations, the antibody is a fragment of a 2A4 or 7D8 antibody, including chimeric and humanized versions thereof, such as a Fab fragment, a Fab' fragment, a $F(ab')_2$ fragment, a Fv fragment or a ScFv fragment.

In some aspects of the invention, the antibody specifically binds to aggregated amyloid protein without specifically binding to monomeric amyloid protein (e.g., at least a 10-fold and usually at least 100-fold lower specific binding affinity for monomeric forms of the amyloid protein).

In some formulations, the antibody is present at a concentration within the range from about 5 mg/mL to about 100 mg/mL. In some formulations, the antibody is present at a concentration within the range from about 5 mg/mL to about 15 mg/mL. In some formulations, the antibody is present at a concentration within the range from about 25 mg/mL to about 75 mg/mL. For example, the antibody may be present at a concentration of about 10 mg/mL, or present at a concentration of about 50 mg/mL. The antibody may be present in a sterile liquid dosage form of about 50 mg/vial to about 500 mg/vial, or greater. For example, the antibody may be present in a sterile liquid dosage form of about 100 mg/vial.

Antibodies used in the disclosed formulations can be coupled with a therapeutic moiety, such as a cytotoxic agent, a radiotherapeutic agent, an immunomodulator, a second antibody (e.g., to form an antibody heteroconjugate), or any other biologically active agent that facilitates or enhances the activity of a chimeric or humanized 2A4 or a chimeric or humanized 7D8 antibody. Representative therapeutic moieties include agent known to be useful for treatment, management, or amelioration of amyloid disease or symptoms of amyloid disease.

Antibodies used in the disclosed formulations can also be coupled with a detectable label, for example, as useful for diagnosing an amyloid disorder, for monitoring progression of amyloid disease, and/or for assessing efficacy of treatment. Antibodies formulated as described are particularly useful for performing such determinations in subjects having or being susceptible to AA amyloidosis or AL amyloidosis, or in appropriate biological samples obtained from such subjects. Representative detectable labels that may be coupled or linked to a humanized 2A4 antibody or humanized 7D8 antibody include various enzymes, such as horseradish peroxidase, alkaline phosphatase, beta-galactosidase, or acetylcholinesterase; prosthetic groups, such streptavidinlbiotin and avidin/biotin; fluorescent materials, such as but umbelliferone, fluorescein, fluorescein isothiocynate, rhodamine, dichlorotriazinylamine fluorescein, dansyl chloride or phycoerythrin; luminescent materials, such as luminol; bioluminescent materials, such as luciferase, luciferin, and aequorin; radioactive materials, such as but not limited to iodine ($^{131}I$, $^{125}I$, $^{123}I$, $^{121}I$), carbon ($^{14}C$), sulfur ($^{5}S$), tritium ($^{3}H$), indium ($^{115}In$, $^{113}In$, $^{112}In$, $^{111}In$), and technetium ($^{99}Tc$), thallium ($^{201}Ti$), gallium ($^{68}Ga$, $^{67}Ga$), palladium ($^{103}Pd$), molybdenum ($^{99}Mo$), xenon ($^{133}Xe$), fluorine ($^{18}F$), $^{153}Sm$, $^{177}Lu$, $^{159}Gd$, $^{149}Pm$, $^{140}La$, $^{175}Yb$, $^{166}Ho$, $^{90}Y$, $^{47}Sc$, $^{186}Re$, $^{188}Re$, $^{142}Pr$, $^{105}Rh$, $^{97}Ru$, $^{68}Ge$, $^{57}Co$, $^{65}Zn$, $^{85}Sr$, $^{32}P$, $^{153}Gd$, $^{169}Yb$, $^{51}Cr$, $^{54}Mn$, $^{75}Se$, $^{113}Sn$, and $^{117}Tin$; positron emitting metals using various positron emission tomographies, nonradioactive paramagnetic metal ions, and molecules that are radiolabelled or conjugated to specific radioisotopes.

Therapeutic moieties and/or detectable substances may be coupled or conjugated directly to a murine, chimeric or humanized 2A4 antibody or a murine, chimeric or humanized 7D8 antibody, or indirectly, through an intermediate (e.g., a linker) using techniques known in the art. See e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., *Immunol. Rev.,* 1982, 62:119-58.

Antibodies used in the disclosed formulations also include modified forms of murine, chimeric or humanized 2A4 antibodies, or murine, chimeric or humanized 7D8 antibodies, which have increased in vivo half-lives relative to the corresponding unmodified antibodies. Such modified forms may be prepared, for example, by glycosylation, acetylation, pegylation, phosphorylation, amidation, derivatization by known protecting/blocking groups, proteolytic cleavage, linkage to a cellular ligand or other protein, etc. As one example, representative methods for antibody half-life extension are described in PCT International Publication No. WO 02/060919.

The present invention encompasses antibody formulations having stability at 38° C.-42° C. as assessed by high performance size exclusion chromatography (HPSEC) for at least about 30 days, formulations having stability at 20° C.-24° C. for at least about 1 year, and formulations having stability at 2° C.-4° C. for at least about 3 years. More particularly, the disclosed formulations exhibit low to undetectable levels of antibody aggregation and/or fragmentation, or a low or undetectable increase of antibody fragmentation and/or aggregation above an initial level (e.g., less than about 10% aggregation. A formulation having low to undetectable levels of fragmentation contains at least about 80%, 85%, 90%, 95%, 98%, or 99%, of the total protein, for example, in a single peak as determined by high performance size exclusion chromatography (HPSEC), or in two (2) peaks (one corresponding to each of the antibody heavy chains and antibody light chains) by reduced Capillary Gel Electrophoresis (rCGE), representing the non-degraded antibody, and containing no other single peaks having more than 5%, more than 4%, more than 3%, more than 2%, more than 1%, or more than 0.5% of the total protein each. A formulation having low to undetectable levels of aggregation contains no more than about 15%, no more than about 10%, no more that about 5%, no more than about 4%, no more than about 3%, no more than about 2%, no more than about 1%, or no more than about 0.5% aggregation by weight protein as measured by high performance size exclusion chromatography (HPSEC). For example, in some formulations, less than about 10% of the anti-amyloid antibody is present as an aggregate. Stable formulations of the invention also show little or no loss of biological activity(ies) of a chimeric or humanized 2A4 or chimeric or humanized 7D8, for example binding affinity measurable by ELISAs and/or additional functional assays, such as at least about at least about 50%, 55%, 60%, 65%, 70%, 75%, 80%, 85%, 90%, 95%, 98%, or 99% of an initial measurable value of a given activity.

The histidine buffer may be present in some formulations at a concentration of about 25 mM. In some formulations, the histidine buffer comprises L-histidine and L-histidine HCl monohydrate. For example, in some formulations, L-histidine is present at a concentration within the range from about 16 mM to about 22 mM and L-histidine HCl monohydrate is present at a concentration within the range from about 4 mM to about 8 mM.

In some formulations, trehalose is present at a concentration from about 210 mM to about 250 mM, for example, about 230 mM. In some formulations, a different non-reducing sugar is used, such as sucrose, mannitol, or sorbitol.

In some formulations, polysorbate 20 is present at a concentration within the range of about from about 0.005% to about 0.05% by weight, for example, 0.005%, 0.01%, 0.015%, 0.02%, 0.025%, 0.03%, 0.035%, 0.04%, 0.045%, or 0.05%. Alternatively, in some formulations, polysorbate 20 is present at a concentration within the range of about from about 0.05 g/L, 0.1 g/L, 0.15 g/L, 0.2 g/L, 0.25 g/L, 0.3 g/L, 0.35 g/L, 0.4 g/L, 0.45 g/L, or 0.5 g/L. Some formulations include polysorbate 20 at a concentration of 0.2 g/L.

Some formulations are characterized by a pH within the range of about 6-7, for example, a pH of 6.0, 6.1, 6.2, 6.3, 6.4, 6.5, 6.6, 6.7, 6.8, 6.9, or 7.0. Some formulations have a pH of about 6.5.

Some formulations are characterized by an osmolality of about 300 mOsm/kg.

A bulking agent may also be included some formulations.

Typically, the formulations are sterile, for example, as accomplished by sterile filtration using a 0.2 μm or a 0.22 μm filter. The formulations of the invention are also generally stable upon freezing and thawing.

Optionally, formulations of the invention may further comprise other excipients, such as saccharides, polyols, and amino acids (e.g., arginine, lysine, and methionine). In other aspects, the present invention also provides formulations substantially free of surfactant, inorganic salts, additional sugars, and/or other excipients, i.e., less than about less than 0.0005%, less than 0.0003%, or less than 0.0001% of such compounds.

An exemplary formulation comprises an antibody comprising a light chain comprising an amino acid sequence set forth as SEQ ID NO: 13 and a heavy chain comprising an amino acid sequence set forth as any one of SEQ ID NOs: 14, 15, or 16, which is present at a concentration of about 10 mg/mL, a histidine buffer present at a concentration of about 25 mM, trehalose present at a concentration of about 230 mM; polysorbate 20 present at a concentration of about 0.2 g/L, and a pH of about 6.5.

I.B. Preparation of Pharmaceutical Formulations

The present invention also provides methods of preparing pharmaceutical formulations. In one aspect of the invention, such a method comprises (a) culturing mammalian cells having stably incorporated into their genome nucleic acids encoding the light and heavy chains of murine antibody 2A4 (ATCC Accession Number PTA-9662) or of antibody 7D8 (ATCC Accession Number PTA-9468), or of chimeric or humanized versions thereof, so that the cells secrete the antibody into the cell culture media, and purifying the antibody from the cell culture media; (b) and preparing a formulation comprising (i) the purified antibody present at a concentration within the range from about 1 mg/mL to about 100 mg/mL; (ii) histidine buffer present at a concentration within the range from about 20 mM to about 30 mM; (iii) trehalose present at a concentration within the range from about 210 mM to about 250 mM; and (iv) polysorbate 20 present at a concentration within the range from about 0.005% to about 0.05% by weight; wherein the formulation is characterized by a pH within the range from about 6 to about 7.

In some aspects of the invention, the disclosed methods of preparing a pharmaceutical formulation include the additional step of evaluating at least one property of antibody in the formulation selected from the group consisting of the physical stability, chemical stability and biological activity.

For example, in one aspect of the invention, mammalian cells are cultured for the production of antibodies, wherein the mammalian cells have stably incorporated into their genomes nucleic acids encoding the light and heavy chains of a humanized 2A4 antibody. Mammalian cells useful for this purpose include (a) host cells having stably incorporated into their genomes a nucleic acid sequence encoding a humanized 2A4 light chain set forth as SEQ ID NO: 13 or 21 and a humanized 2A heavy chain set forth as SEQ ID NO: 15 or 24; (b) host cells having stably incorporated into their genomes a nucleic acid having the nucleotide sequence of SEQ ID NO: 19 and a nucleic acid having the nucleotide sequence of SEQ ID NO: 22; and (c) host cells having stably incorporated into their genomes a nucleic acid having the nucleotide sequence of SEQ ID NO: 20 and a nucleic acid having the nucleotide sequence of SEQ ID NO: 23.

For the production of antibodies, the disclosed nucleic acids are included in a vector. In some examples, the vector contains the nucleic acid encoding murine 2A4 of 7D8 antibody, or a chimeric or humanized version thereof, operably linked to a suitable control sequence capable of effecting the expression of the DNA in a host cell. Such control sequences include a promoter to effect transcription (e.g., a constitutive promoter or inducible promoter as known in the art), an optional operator sequence to control such transcription, a sequence encoding suitable mRNA ribosome binding sites, enhancers, polyadenylation signals, and sequences to control the termination of transcription and translation. The vector may be a plasmid, a phage particle (e.g., a viral vector such as adenovirus, adeno-associated-virus, retrovirus, herpes virus, vaccinia virus, lentivirus, poxvirus and cytomegalovirus vectors), or simply a genomic insert. Once transformed into a suitable host, the antibody nucleic acids may integrate into the genome of the host, or the vector may replicate and function independently of the host genome.

The disclosed nucleic acids are included in a vector either singly or in combination (e.g., a combination of a nucleic acid encoding an antibody light chain and a nucleic acid encoding an antibody heavy chain). For example, a vector can comprise a nucleic acid comprising a nucleotide sequence encoding any one of SEQ ID NOs: 13-16, 21, or 24; a nucleic acid comprising the nucleotide sequence of any one of SEQ ID NOs: 19-20 and 22-23, or combinations thereof. Representative vectors of the invention include (a) a vector comprising a nucleic acid sequence encoding a humanized 2A4 light chain set forth as SEQ ID NO: 13 and a humanized 2A heavy chain set forth as SEQ ID NO: 15; (b) a vector comprising a nucleic acid having the nucleotide sequence of SEQ ID NO: 19 and a nucleic acid having the nucleotide sequence of SEQ ID NO: 22; and (c) a vector comprising a nucleic acid having the nucleotide sequence of SEQ ID NO: 20 and a nucleic acid having the nucleotide sequence of SEQ ID NO: 23.

Host cells useful for preparing antibody formulations of the invention include mammalian cells, including cells of human origin, such as monkey kidney cells, human embryonic kidney cells, baby hamster kidney (BHK) cells, Chinese hamster ovary cells (CHO) cells, mouse sertoli cells, human cervical carcinoma (HeLa) cells, canine kidney cells, human lung cells, human liver cells, mouse mammary tumor cells, and NS0 cells. For example, a host cell can comprise in its genome a stably integrated nucleic acid comprising a nucleotide sequence encoding any one of SEQ ID NOs: 13-16, 21, and 24; a stably integrated nucleic acid comprising the nucleotide sequence of any one of SEQ ID NOs: 19-20 and 22-23, or combinations thereof. Representative host cells of the invention include (a) host cells comprising a nucleic acid sequence encoding a humanized 2A4 light chain set forth as SEQ ID NO: 13 or 21 and a humanized 2A heavy chain set forth as SEQ ID NO: 15 or 24; (b) host cells comprising a nucleic acid having the nucleotide sequence of SEQ ID NO: 19 and a nucleic acid having the nucleotide sequence of SEQ ID NO: 22; and (c) host cells comprising a nucleic acid having the nucleotide sequence of SEQ ID NO: 20 and a nucleic acid having the nucleotide sequence of SEQ ID NO: 23.

In another aspect of the invention, a chimeric or humanized 2A4 antibody or a chimeric or humanized 7D8 antibody is prepared by chemical synthesis and then used in the disclosed formulations.

Antibodies used to prepare the disclosed formulations are typically isolated or purified, i.e., substantially free of cellular material or other contaminating proteins from the cells in which they are produced, or substantially free of chemical precursors or other chemicals when chemically synthesized. For example, an antibody that is substantially free of cellular material includes preparations of the antibody having less than about 30%, 25%, 20%, 15%, 10%, 8%, 5%, 2%, 1%, 0.5%, 0.1%, or less (by dry weight) of contaminating protein. When an antibody is recombinantly produced, it is also substantially free of culture medium such that culture medium represents less than about 30%, 25%, 20%, 15%, 10%, 8%, 5%, 2%, 1%, 0.5%, 0.1%, or less, of the volume of the protein preparation. When an antibody is produced by chemical synthesis, it is preferably substantially free of or separated from chemical precursors or other chemicals involved in the synthesis of the protein. Accordingly, such antibody preparations have less than about 30%, 25%, 20%, 15%, 10%, 8%, 5%, 2%, 1%, 0.5%, 0.1%, or less (by dry weight) of chemical precursors or compounds other than the antibody drug substance. Purification of recombinantly expressed antibody can utilize any of a number of methods known in the art, such as, for example, affinity chromatography, acid treatment, depth filtration, anion exchange chromatography, cation exchange chromatography, nanofiltration, ultrafiltration, dialysis and diafiltration.

The purified antibody drug substance can be adjusted to a solution comprising any of the formulations described herein, diluted to the desired concentration and stored until ready for use. Optionally, the formulation can be stored in concentrated form until ready for use. Liquid formulations can be stored in frozen form, under refrigeration or at room temperature, depending upon their stability profile, which can be determined empirically. In some instances a further filtration step is applied. Some of the formulations described herein may be lyophilized and stored in powder form. Lyophilized formulations can be stored in frozen form, under refrigeration or at room temperature, depending upon their stability profile, which can be determined empirically. For example, the lyophilized formulations can be stored at a temperature of about 2° C. to 8° C. In such cases, the formulation would be reconstituted prior to administration to a patient to yield a liquid formulation having the antibody and excipients present in the concentrations described herein. In some cases, the formulation is reconstituted in sterile water. In some cases, the formulation is reconstituted and added to an infusion bag for administration to the patient. The reconstituted formulation can be stored under refrigeration or at room temperature prior to administration to a patient for a time consistent with the stability profile. Lyophilization and reconstitution techniques are known in the art and described in the Examples.

Thus, the present invention also encompasses pharmaceutical products comprising lyophilized antibody drug substance and instructions for reconstitution and use. For example, a representative pharmaceutical product can comprise: (a) a vial comprising about 100 mg antibody in powder form; (b) instructions for reconstitution of the antibody; and (c) instructions for preparing the reconstituted antibody for infusion, wherein (i) the antibody comprises a light chain comprising an amino acid sequence set forth as SEQ ID NO: 13 and a heavy chain comprising an amino acid sequence set forth as any one of SEQ ID NOs: 14-16; and (ii) the reconstitution instructions require reconstitution with water for injection to an extractable volume of 10 mL.

II. Methods of Diagnosis and Treatment

Also provided are methods of therapeutically or prophylactically treating a human patient having or at risk of having amyloidosis characterized by the presence of amyloid protein fibrils, the method comprising administering to the patient an effective dosage of any of the formulations described herein.

II.A. Subjects Amenable to Diagnosis and Treatment

Humanized 2A4 drug substance is to be used for the treatment of systemic amyloidosis, such as amyloidoses involving either amyloid light chain AL or amyloid A (AA) proteins. Systemic amyloidoses are a complex group of diseases caused by tissue deposition of misfolded proteins that result in progressive organ damage. The most common type, AL amyloidosis or primary amyloidosis, involves a hematological disorder caused by clonal plasma cells that produce misfolded immunoglobulin light chains. Overproduction of misfolded light chain by plasma cells results in deposits of abnormal AL protein (amyloid), in the tissues and organs of individuals with AL amyloidosis. Clinical features of AL amyloidosis include a constellation of symptoms and organ dysfunction that can include cardiac, renal, and hepatic dysfunction, GI involvement, neuropathy's and macroglossia. A different form of systemic amyloidosis, AA amyloidosis or secondary amyloidosis, occurs "secondarily" as a result of other illness, such as chronic inflammatory diseases (for example, rheumatoid arthritis and ankylosing spondylitis) or chronic infections (for example, tuberculosis or osteomyelitis). In secondary amyloidosis, the depositing amyloid protein is amyloid A protein, derived from an acute-phase protein serum amyloid A.

Peripheral amyloidosis is be amenable to this type of amyloid-specific immunotherapy through antibody targeting of a neo-epitope that has been identified in AA amyloid, as well as in AL amyloid. Studies in animal models of both AA and AL have demonstrated that significant positive therapeutic effects may be possible at reasonable doses of antibody.

Subjects or patients amenable to treatment using the disclosed antibody formulations include individuals at risk of disease but not showing symptoms, as well as patients presently showing symptoms of amyloid disease. Therefore, the present methods can be administered prophylactically to the general population without the need for any assessment of the risk of the subject patient. For example, the present methods are especially useful for individuals who do have a known genetic risk autoimmune disorders. Such individuals include those having relatives who have experienced this disease and those whose risk is determined by analysis of genetic or biochemical markers. As another example, patients suffering from AA amyloidosis can be asymptomatic for a prolonged period of time, such that clinical diagnosis of AA amyloidosis is often delayed or missed until the amyloid deposits are extensive. For those patients who are symptomatic, it is estimated that only 53% of the cases are diagnosed. See e.g., L.E.K. Consulting, Independent Market Research (2003). Prophylactic administration disclosed antibody formulations may reduce the incidence of AA amyloidosis.

The present methods are especially useful for individuals who do have a known risk of, are suspected to have, or have been diagnosed with AA amyloidosis or AL amyloidosis. Such individuals include but are not limited to those having chronic inflammatory diseases, inherited inflammatory diseases, and chronic microbial infections, such as rheumatoid arthritis, juvenile chronic arthritis, ankylosing spondylitis, psoriasis, psoriatic arthropathy, Reiter's syndrome, Adult Still's disease, Behcet's syndrome, Crohn's disease, Familial Mediterranean Fever, leprosy, tuberculosis, bronchiectasis, decubitus ulcers, chronic pyelonephritis, osteomyelitis, Whipple's disease, myeloma, macroglobulinemia, immunocyte dyscrasia, monoclonal gammopathy, occult dyscrasia. Chronic inflammatory and infectious conditions are prerequisite to the development of AA amyloidosis and AL amyloidosis manifested by local nodular amyloidosis can be associated with chronic inflammatory diseases. Individuals who do have known risk of AA amyloidosis also include but are not limited to those having malignant neoplasms as Hodgkin's lymphoma, renal carcinoma, carcinomas of gut, lung and urogenital tract, basal cell carcinoma, and hairy cell leukemia. Additionally, individuals with known risk of AA amyloidosis also include but are not limited to those having lymphoproliferative disorders such as Castleman's Disease. Some of such patients have AA amyloidosis characterized by the presence of amyloid A protein fibrils. Some of such patients have AL amyloidosis characterized by the presence of amyloid light chain-type protein fibrils. Some patients have systemic organ dysfunction attributed to AL amyloidosis, including dysfunction of the heart, kidney, liver, peripheral nervous system, gastrointestinal system, autonomic nervous system, lung, and/or soft tissue or lymphatic system.

Patients amenable to treatment also include those patients who have received, are currently receiving, or will later receive an alternate therapy, for treatment of amyloid disease or an associated condition, such as, inflammatory diseases, chronic microbial infections, malignant neoplasms, inherited inflammatory diseases, and lymphoproliferative disorders. For example, patients may also receive or have received one or more of the therapeutic agents identified herein with respect to combination therapies. As a particular example, patients suffering from AL may also receive or have received bortezomib, melphalan, lenalidomide and/or carfilzomib. For those patients who have previously received alternate therapies for the treatment of amyloid disease, such therapies may or may not have been successful by the relevant clinical measures.

II.B. Treatment Regimes

As used herein, the terms "treat" and "treatment" refer to the alleviation or amelioration of one or more symptoms or effects associated with the disease, prevention, inhibition or delay of the onset of one or more symptoms or effects of the disease, lessening of the severity or frequency of one or more symptoms or effects of the disease, and/or increasing or trending toward desired outcomes as described herein.

Desired outcomes of the treatments disclosed herein vary according to the amyloid disease and patient profile and are readily determinable to those skilled in the art. Generally, desired outcomes include measurable indices such as reduction or clearance of pathologic amyloid fibrils, decreased or inhibited amyloid aggregation and/or deposition of amyloid fibrils, and increased immune response to pathologic and/or aggregated amyloid fibrils. Desired outcomes also include amelioration of amyloid disease-specific symptoms. For example, desired outcomes for the treatment of AL amyloidosis include a decrease in the incidence or severity of known symptoms, including organ dysfunction, peripheral and autonomic neuropathy, carpal tunnel syndrome, macroglossia, restrictive cardiomyopathy, arthropathy of large joints, immune dyscrasias, myelomas, as well as occult dyscrasias. As another example, desired outcomes for the treatment of AA include a decrease in associated inflammation, arthritis, psoriasis, microbial infection, malignancy, or symptoms of other preexisting or coexisting disease to which the AA amyloidosis is secondary.

Desired outcomes of the disclosed therapies are generally quantifiable measures as compared to a control or baseline measurement. As used herein, relative terms such as "improve," "increase," or "reduce" indicate values relative to a control, such as a measurement in the same individual prior to initiation of treatment described herein, or a measurement in a control individual or group. A control individual is an individual afflicted with the same amyloid disease as the individual being treated, who is about the same age as the individual being treated (to ensure that the stages of the disease in the treated individual and the control individual are comparable), but who has not received treatment using the disclosed antibody formulations. In this case, efficacy of the disclosed antibody formulations is assessed by a shift or trend away from measurable indices in the untreated control. Alternatively, a control individual is a healthy individual, who is about the same age as the individual being treated. In this case, efficacy of the disclosed antibody formulations is assessed by a shift or trend toward from measurable indices in the healthy control. Changes or improvements in response to therapy are generally statistically significant and described by a p-value less than or equal to 0.1, less than 0.05, less than 0.01, less than 0.005, or less than 0.001 may be regarded as significant.

In both asymptomatic and symptomatic patients, treatment according to the disclosed methods can begin at any time before or after the diagnosis of the underlying AA or AL amyloid diseases. Treatment typically entails multiple dosages over a period of time. Treatment can be monitored by assaying antibody, or employing radiolabeled SAP Scintigraphy over time. If the response falls, a booster dosage may be indicated. The response of patients with AL amyloidosis to treatment can be monitored by assessing cardiac markers, such as NT-proBNP and/or troponin, serum creatine, and/or alkaline phosphatase; by performing serum free light chain (SFLC) assays, quantitative immunoglobulin assays, biopsies, serum protein electrophoresis (SPEP), urine protein electrophoresis (UPEP), serum, urine immunofixation electrophoresis (IFE), and/or organ imaging techniques. An exemplary complete response (CR) can be determined from response criteria including negative IFE of serum and urine, normal κ/λ ration and/or <5% plasma cells in bone marrow. An exemplary very good partial response (VGPR) can be determined from a dFLC of <40 mg/L. An exemplary partial response (PR) can be determined from a dFLC decrease of ≥50%. In the kidney, a response to treatment can be determined, for example, from a ≥50% reduction (e.g., >0.5 g/24 hours) in 24 hour urine protein excretion in the absence of either a reduction in eGFR of ≥25% or an increase in serum creatine of ≥0.5 mg/dL. In the liver, a response to treatment can be determined, for example, from a ≥50% reduction in initially elevated alkaline phosphatase or a ≥2 cm reduction in liver size on CT scan or MRI. In the heart, a response to treatment can be determined, for example, from a ≥30% and 300 ng/L reduction in NT-proBNP in patients with baseline of NT-proBNP of >650 ng/L.

The antibody formulation can be administered intravenously in dosage ranges from about 10 mg to about 5000 mg for the patient in question, such as, for example, about 10 mg, about 30 mg, about 100 mg, about 300 mg, about 1000 mg, about 2000 mg, or about 2500 mg. The antibody formulation can also be administered intravenously in dosage ranges from about 0.1 mg/kg to about 50 mg/kg, or from about 0.5 mg/kg to about 30 mg/kg, of the host body weight. For example, dosages can be about 0.5 mg/kg body weight, about 1.0 mg/kg, about 1.5 mg/kg, about 2.0 mg/kg, about 4.0 mg/kg, about 5.0 mg/kg, about 8.0 mg/kg, about 10 mg/kg, about 15 mg/kg, about 16 mg/kg, about 20 mg/kg, about 25 mg/kg, or about 30 mg/kg body weight. Dose escalation for an individual patient can occur at the discretion of the prescriber in the absence of any clinically significant occurrence that the prescriber might reasonably believe would present an undue safety risk for the patient, such as, for example, Grade ≥3 non-hematologic toxicity, Grade ≥3 nausea, vomiting or diarrhea uncontrolled by maximum antiemetic/anti-diarrhea therapy, Grade 4 neutropenia lasting >7 days in the absence of growth factor support, Grade 3 or 4 neutropenia of any duration accompanied with fever ≥38.5° C. and/or systemic infection, or other Grade ≥4 hematologic toxicity.

Antibody is usually administered on multiple occasions. An exemplary treatment regime entails administration once per every two weeks, once a month, or once every 3 to 6 months. For example, patients can receive the antibody formulation once every four weeks as a cycle, for example every twenty-eight days. The dosing frequency can be adjusted depending on the pharmacokinetic profile of the antibody formulation in the patient. For example, the half-life of the antibody may warrant a two week frequency of dosing. In some methods, two or more monoclonal antibodies with different binding specificities are administered simultaneously, in which case the dosage of each antibody administered falls within the ranges indicated. Intervals between single dosages can be weekly, monthly or yearly. Intervals can also be irregular as indicated by measuring blood levels of antibody to amyloid protein (e.g., AA) in the patient. In some methods, dosage is adjusted to achieve a plasma antibody concentration of about 1-1000 µg/ml or about 25-300 µg/ml. Alternatively, antibody can be administered as a sustained release formulation, in which case less frequent administration is required.

Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, until a partial or complete response is achieved, and/or until the patient shows lessening or amelioration of symptoms of disease. Thereafter, the patent can be administered a prophylactic regime.

The formulations disclosed herein may be provided in a dosage form that is suitable for parenteral (e.g., intravenous, intramuscular, subcutaneous) administration. As appropriate for particular applications, the formulation may be alternately provided in a dosage suitable for rectal, transdermal, nasal, vaginal, inhalant, ocular or other administration. The pharmaceutical formulations are typically prepared according to conventional pharmaceutical practice. See e.g., Remington: The Science and Practice of Pharmacy, (19th ed.) ed. A. R. Gennaro, 1995, Mack Publishing Company, Easton, Pa. and Encyclopedia of Pharmaceutical Technology, eds. J. Swarbrick and J. C. Boylan, 1988-1999, Marcel Dekker, N.Y.

In one aspect of the invention, a method of therapeutically or prophylactically treating a human patient having or at risk for having light chain (AL) amyloidosis characterized by the presence of amyloid fibrils, deposits or prefibrillar aggregates, comprises administering to the patient an effective dosage of a pharmaceutical formulation comprising: (a) an antibody comprising a light chain comprising an amino acid sequence set forth as SEQ ID NO: 13 and a heavy chain comprising an amino acid sequence set forth as any one of SEQ ID NOs: 14-16, and which is present at a concentration of about 10 mg/mL; (b) a histidine buffer present at a concentration of about 25 mM; (c) trehalose present at a concentration of about 230 mM; (d) polysorbate 20 present at a concentration of about 0.2 g/L; and (e) a pH of about 6.5. In such a method, the dosage is typically from about 0.5 mg/kg to about 30 mg/kg of the antibody (e.g., about 0.5 mg/kg to about 8 mg/kg, or about 8 mg/kg to about 30 mg/kg) administered intravenously or subcutaneously at a frequency of from about weekly to about quarterly (e.g., once every 28 days).

II.C. Combinational Drug Therapy Treatment Regimes

The present invention also encompasses combination therapies for treatment or prophylaxis of amyloid disease, particularly AA amyloidosis and AL amyloidosis. Such combination therapies are performed by administering an antibody formulation of the invention in conjunction with one or more second therapeutic agents, such as another therapy to treat or effect prophylaxis of AA amyloidosis or AL amyloidosis, as the case may be. Combination therapy according to the invention may also be performed in conjunction with a second therapy is used to treat or effect prophylaxis of a disease or condition associated with amyloid disease, such as an inflammatory disease, a chronic microbial infection, a neoplasm (including malignant neoplasms), an inherited inflammatory disease, and/or a lymphoproliferative disorder. Numerous treatments are available in commercial use, in clinical evaluation, and in pre-clinical development, any of which could be selected for use in combination with the disclosed antibody formulations. Such treatments can be one or more compounds or treatments selected from, but not limited to several major categories, namely, (i) non-steroidal anti-inflammatory drugs (NSAIDs; e.g., detoprofen, diclofenac, diflunisal, etodolac, fenoprofen, flurbiprofen, ibuprofen, indomethacin, ketoprofen, meclofenameate, mefenamic acid, meloxicam, nabumeone, naproxen sodium, oxaprozin, piroxicam, sulindac, tolmetin, celecoxib, rofecoxib, aspirin, choline salicylate, salsalte, and sodium and magnesium salicylate); (ii) steroids (e.g., cortisone, dexamethasone, hydrocortisone, methylprednisolone, prednisolone, prednisone, triamcinolone); (iii) DMARDs, i.e., disease modifying antirheumatic drugs (e.g., cyclosporine, azathioprine, methotrexate, leflunomide, cyclophosphamide, hydroxychloroquine, sulfasalazine, D-penicillamine, minocycline, and gold); (iv) recombinant proteins (e.g., ENBREL® (etanercept, a soluble TNF receptor) and REMICADE® (infliximab) a chimeric monoclonal anti-TNF antibody); (v) stem cell transplantation; and/or (vi) chemotherapy. Patients with AL amyloidosis may also receive treatment regimes that include drugs or combinations of drugs often used to treat hematological malignancies, such as melphalan, prednisone, dexamethasone, lenalidomide (REVLIMID®) and proteosome inhibitors such as bortezomib (VELCADE®), and carfilzomib (KYPROLIS™), at dosages in the range of the standard of care.

The duration of the combination therapy depends on the type of amyloid disease being treated, any underlying disease associated with the amyloid disease, the age and condition of the patient, the stage and type of the patient's disease, how the patient responds to the treatment, etc. A medical doctor can observe the therapy's effects closely and make any adjustments as needed. Additionally, a person having a greater risk of developing AA amyloidosis (e.g., a person who is genetically predisposed or previously had an inflammatory disorder or other underlying diseases) or AL amyloidosis may receive prophylactic combination treatments to inhibit or delay the development of AA AL aggregates such as fibrils, or as maintenance therapy post-treatment.

When performing a combination therapy, the two or more drug substances are administered simultaneously or sequentially in any order, i.e., a formulation of the invention is administered prior to administering a second drug substance, concurrently with a second drug substance, or subsequent to administration of a second drug substance. For example, a combination therapy may be performed by administering a first therapy prior to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) administering a second agent/therapy.

The dosage, frequency and mode of administration of each component of the combination can be controlled independently. For example, one therapeutic agent/therapy may be administered orally three times per day, while the second therapeutic agent/therapy may be administered intramuscularly once per day. Combination therapy may be given in on-and-off cycles that include rest periods. The compounds may also be admixed or otherwise formulated together such that one administration delivers both compounds. In this case, each therapeutic agent is generally present in an amount of 1-95% by weight of the total weight of the composition. Alternatively, an antibody formulation of the invention and a second therapeutic agent can be formulated separately and in individual dosage amounts. Drug combinations for treatment can be provided as components of a pharmaceutical pack.

Preferably, the disclosed combination therapies elicit a synergistic therapeutic effect, i.e., an effect greater than the sum of their individual effects or therapeutic outcomes. Measurable therapeutic outcomes are described herein. For example, a synergistic therapeutic effect may be an effect of at least about two-fold greater than sum of the therapeutic effects elicited by the single agents of a given combination, or at least about five-fold greater, or at least about ten-fold greater, or at least about twenty-fold greater, or at least about fifty-fold greater, or at least about one hundred-fold greater. A synergistic therapeutic effect may also be observed as an increase in therapeutic effect of at least 10% compared to the sum of the therapeutic effects elicited by the single agents of a given combination, or at least 20%, or at least 30%, or at least 40%, or at least 50%, or at least 60%, or at least 70%, or at least 80%, or at least 90%, or at least 100%, or more. A synergistic effect is also an effect that permits reduced dosing of therapeutic agents when they are used in combination.

EXAMPLES

The following examples have been included to illustrate modes of the invention. Certain aspects of the following examples are described in terms of techniques and procedures found or contemplated by the present co-inventors to work well in the practice of the invention. In light of the present disclosure and the general level of skill in the art, those of skill appreciate that the following examples are intended to be exemplary only and that numerous changes, modifications, and alterations may be employed without departing from the scope of the invention.

Example 1. Selection of Humanized 2A4 for the Treatment of AL Amyloidosis

An IgG1, kappa isotype antibody was prepared, which is a humanized version of murine antibody 2A4. The light chain and heavy chain sequences of representative humanized 2A4 antibodies are set forth in FIGS. 1A-1B and 3. Nucleic acids encoding the particular humanized 2A4 antibody version 3, which amino acid sequences are shown in FIG. 3, are depicted in FIGS. 4A-4B.

The parent monoclonal 2A4 antibody is directed against a neo-carboxy terminal epitope of human serum Amyloid A (sAA), resulting from cleavage of the native sAA molecule at amino acid residue 76. The murine antibody does not cross-react with IgGs or free light chain (LC) and it has shown broad isotype recognition of patient derived AL amyloid samples examined to date. 2A4 recognizes multiple forms of AL light chain amyloid including soluble multimer and insoluble deposits. In addition, the antibody has been shown to promote regression of amyloidoma in a mouse xenograft model. The light chain and heavy chain sequences of murine 2A4 antibody are set forth in FIG. 2.

Example 2. Dose Determination for Humanized 2A4 Antibody

Nonclinical studies in the TRIAD mouse model and the cynomolgus monkey have utilized doses of 4 and 40 mg/kg in the mouse and 10, 50, and 100 mg/kg in the monkey. Conversion to the Human Equivalent Dose (HED) on a mg/kg basis (most appropriate conversion for monoclonal antibodies due to their restriction to the vascular space) gives HEDs of 0.32 and 3.2 for the mouse and 3.2, 16, and 32 for the monkey. Based on currently available data, the NOAEL in both species is expected to be the highest dose administered. Using a mouse HED (most sensitive species due to dosing limitations) of 3.2 and a 10× safety factor, the MRSD for first in man dosing would be approximately 0.32 mg/kg. Based upon animal studies, administration to humans is begun with a dose of 0.5 mg/kg.

Example 3. Preparation of the Expression Vector

For generation of the final h2A4 IgG1 HC vector the variable region of the heavy chain was isolated by PCR using the plasmid CET1019AS-hygro-h2A4VH3-Sce 4.23.07 as template. Primers used for the amplification introduced at the 5' end of the fragments an MfeI restriction site and at the 3' end a BlpI restriction site for subcloning. The variable region was cloned into the MfeI and BamHI digested eukaryotic expression vector pBI-61, which contains the genomic constant regions of human IgG1 of G1m(3) allotype. The resulting recombinant expression vector pBI-61/2A4 IgG1-REM is 9,015 base pairs in size and carries the selectable marker dihydrofolate reductase (DHFR) from hamster under the control of the DHFR promoter and polyadenylation signal. This vector also contains the beta-lactamase gene for selection in *E. coli* as well as origins of replication for *E. coli* (ColE1 ori), SV40 (SV40 ori) and filamentous phage f1 (f1 ori). Expression of the HC is driven by the immediate early promoter/enhancer region from human cytomegalovirus (CMV) combined with a transcription enhancing element (TE) derived from the hamster genome. For transcript termination and stabilization the polyadenylation signal from hamster growth hormone is used and for enhancement of transcription a non-coding sequence derived from the hamster genome (TE).

Using the plasmid CET1019AS-hu2A4VL3-hck-puro-Sce 4.19.07 as template the variable region of the h2A4 LC was isolated by PCR introducing at the 5' end of the fragments an SgrAI restriction site and at the 3' end a KpnI restriction site for subcloning into the final eukaryotic expression vector pBI-60 digested with the same restriction enzymes. This vector contains the genomic constant region of a human kappa chain. The resulting recombinant expression vector pBI-60/2A4 LC is 7,144 base pairs in size and contains the selectable marker neomycin phosphotransferase mutant, which confers resistance to geneticin, under the control of the SV40 promoter. For transcript termination the polyadenylation signal from Herpes simplex thymidine kinase is used. This vector also contains the beta-lactamase gene for selection in *E. coli* as well as origins of replication for *E. coli* (ColE1 ori) and filamentous phage f1 (f1 ori). Expression of the LC is driven by the immediate early promoter/enhancer region from human cytomegalovirus (CMV) combined with a transcription enhancing element (TE) derived from the hamster genome. For transcript termination and stabilization the polyadenylation signal from hamster growth hormone is used and for enhancement of transcription a non-coding sequence derived from the hamster genome (TE).

Example 4. Production of Humanized 2A4 Antibody (Pool-Derived Material)

Humanized 2A4 was produced in Chinese Hamster Ovary (CHO) cells, grown in chemically defined media without any bovine-derived components. Antibody was pooled from stable transfected cells from which the production cell line was ultimately derived. The pool-derived material was purified by protein A-affinity chromatography. This material was used for human tissue cross-reactivity studies and for a single dose pharmacokinetic (PK) study in cynomolgus monkeys. The formulation of the humanized 2A4 antibody is 10 mg/mL antibody, 25 mM L-Histidine/L-Histidine HCl monohydrate, 230 mM Trehalose dehydrate, 0.02% (w/v) Polysorbate (TWEEN®) 20, pH=6.5.

Example 5. Production of Humanized 2A4 Antibody (Clone-Derived Material)

A single CHO cell clone was isolated from cell pools as described in Example 3, and was used to establish the Master Cell Bank (MCB) without any bovine materials. Humanized 2A4 for nonclinical studies was manufactured at 80 L scale using the same cell cultivation and purification processes (except scale-up modifications) as the GMP clinical version of humanized 2A4 (2,000 L scale). Material from the 2,000 L scale production may also be used in nonclinical studies.

Example 6. Process of Manufacturing Humanized 2A4 Antibody

Vial Thaw & Inoculum Expansion.

Cells from the MCB are thawed and transferred into an appropriate cell culture flask. The cells are incubated at approximately 37° C. The thawed culture is propagated for one to four days (first passage after cell thaw). For sub-cultivation, an aliquot of a grown cell culture (and a defined volume of pre-warmed, 0.22 μm or less filtered inoculum medium) is used to reach a seed density of approximately 0.1-0.5×10$^6$ cells/mL in standard cell culture vessels of approximately 0.02 L to 1 L working volume. As an example, the first passages can be done in 0.125 L or 0.25 L or 0.5 L vessels, followed by passages in 1 L vessels. A stock culture can be initiated at this cultivation stage. For preparation of inoculum cultures for individual production fermenters, aliquots of the stock cultures are expanded to generate cultures with up to 25 L volume. Typically, the cell culture is scaled up from 1 L cultures to 2 or more 1 L or 2 L cultures, then to 2 or more 2 L or 3 L cultures and finally to 2 or more cultures with up to 25 L culture volume per vessel. Grown cell suspensions from several vessels can be pooled and used to inoculate the 80 L bioreactor. Shake flasks, T-flasks, spinner flasks and bags can be used as standard cell culture vessels for the above cultivation steps.

Seed Cultures in Bioreactors.

Before inoculation with cells, 0.22 µm or less filtered growth medium is added to the bioreactors. The content of the filled bioreactors is warmed to approximately 37° C. and maintained at this temperature throughout incubation of the cells. Cells from the inoculum cultures are transferred into the pre-warmed medium. The initial cell density is targeted within the range of $0.1$-$0.5 \times 10^6$ cells/mL. The cells are grown in an 80 L bioreactor and subsequently in a 400 L bioreactor. Cells are subcultivated approximately every two to four days. At this stage, cells may be transferred to another vessel of the same or larger volume. Typically, the cell culture is scaled up from 1×80 L bioreactor culture to 1×400 L culture. To initiate the production phase, the cells are transferred from the grown 400 L cell suspension to the production bioreactor of approximately 2,000 L working volume.

Production Culture in 2,000 L Bioreactor.

Before inoculation with cells, 0.22 µm or less filtered production medium is added to the production bioreactor. The content of the filled production bioreactor is warmed to approximately 37° C. and maintained at this temperature throughout incubation of the cells. The initial cell density in the production phase is targeted within the range of $0.1$-$0.5 \times 10^6$ cells/mL. The production bioreactor is run in a fed batch mode. To support the production of antibody and to prolong culture duration, a nutrient feed medium is added during the production stage. The point at which to start feeding is determined either by culture time or by cell density. As needed, a glucose solution and/or glutamine solution can be added during the production stage to avoid depletion of these substances during the production period. The run time of the 2,000 L production bioreactor is typically 8 to 14 days. Pre-harvest samples are tested for sterility, mycoplasma, and adventitious virus in vitro.

Harvest and Clarification.

After 8 to 14 days of cultivation in the production phase, the cell culture fluid is separated from the cells. After pre-harvest sampling and prior to harvest, the pH and the temperature of the culture can be adjusted to facilitate removal of cells, debris and particles during harvest. To remove the cells, the culture is passed through a centrifugation plus dead-end filtration unit. The cells are centrifuged and/or retained by the membranes. The harvested culture fluid is passed through filters of 0.22 µm pore size or less and collected in an appropriate container. Residual culture fluid can be removed from the harvest system by flushing with Phosphate Buffered Saline (PBS) to recover residual product from the harvest system. The resulting recovered product amount is collected together with the harvested culture fluid to form the harvest pool, also called harvested cell-free culture fluid (HCCF). The pH and temperature of the HCCF can be adjusted to facilitate the subsequent downstream processing steps.

Purification.

The antibody is purified from the HCCF by a series of steps involving affinity chromatography, acid treatment, depth filtration, anion exchange chromatography, cation exchange chromatography, nanofiltration and ultra-/diafiltration, several of which may be performed in several cycles. To remove contaminants the affinity chromatography process step specifically binds the antibody product. The HCCF is applied to the chromatography column packed with the MabSelect matrix. The matrix binds antibody at neutral pH, while contaminants appear in the flow through and are removed. The column is eluted in a step elution with a 100 mM acetic acid/sodium acetate solution at pH 3.5. To inactivate potential viral contaminants, the antibody solution is incubated at room temperature for a minimum of 60 minutes at pH 3.5±0.1. After incubation the acid treated pool is adjusted to pH 7.2 using a 2 M Trometamol solution and subjected to depth filtration for clarification. For anion exchange chromatography, the depth filtered product pool is adjusted to a conductivity ≤7 mS/cm with Water for Injection (WFI). The adjusted pool is applied to a chromatography column packed with Q Sepharose FF resin. The antibody passes through the anion exchange matrix unbound. The flow through is monitored and the antibody containing fraction is collected based on absorbance measurement. For cation exchange chromatography, the product pool is adjusted to a pH of 5.5±0.1 by addition of acetic acid up to a conductivity of ≤7.5 mS/cm with WFI. The adjusted product pool is applied onto a chromatography column packed with SP Sepharose FF cation exchange resin. This chromatography step is performed in a bind-elute mode. The antibody binds to the cation exchange matrix. The column is eluted in a step elution with a 100 mM acetic acid/sodium acetate and 138.5 mM sodium chloride solution at pH 5.5. Potential viral contaminants are removed by passing the antibody solution through a 0.1 µm prefilter and a Planova 20N nanofilter at a maximum pressure of 1 bar differential pressure of the Planova 20N nanofilter. During ultrafiltration/diafiltration (UF/DF), the product is concentrated to the target concentration, and the buffer is exchanged with the formulation buffer. Concentration and diafiltration is performed using ultrafiltration membranes having a cut-off of approximately 30 kD. The material is processed by concentrating the product to 30-100 mg/mL. The 30 kD pool is then diafiltered with a solution of 25 mM L-Histidine, pH 6.5 and is flushed to a concentration of about 60-70 mg/mL. The 30 kD pool intermediate may be stored at −40° C. until formulation is performed. For formulation, the 30 kD product pool is adjusted to a solution containing 17.5 mM L-Histidine/7.5 mM L-Histidine Hydrochloride, 230 mM Trehalose, and 0.02% (w/v) Polysorbate20, pH=6.5. The antibody is finally diluted with formulation buffer to the desired target concentration of 10 mg/mL. The resulting drug substance is filtered through a 0.22 µm filter to remove any potential adventitious microbial contaminants and particulate material. The drug substance can be stored frozen at −40° C. until filling.

Example 7. Characterization of Drug Substance Containing Humanized 2A4 Antibody

Humanized 2A4 used for formulation is composed of two heterodimers. Each of the heterodimers is composed of a heavy polypeptide chain of ~50 kDa (449 amino acids) and a kappa light polypeptide chain of ~24 kDa (219 amino acids). The antibody protein has a humanized amino acid sequence with a total molecular mass of approximately 147 kDa. The four polypeptide chains of the antibody molecule are linked together by disulfide bonds. Each heavy polypeptide chain contains one consensus sequence for N-linked glycosylation, which is occupied (positions 299 to 301, highlighted in bold and underlining in FIG. 1A). There are two binding sites for the serum amyloid A epitope per antibody molecule.

A competitive binding ELISA has been established to measure binding of humanized 2A4 to its antigen (CG-GHEDT (SEQ ID NO: 17) when conjugated to Ovalbumin) compared to the reference standard.

Example 8. Humanized 2A4 Drug Substance Components and Composition

The humanized 2A4 drug substance (100 mg/vial) for clinical use is a sterile liquid dosage form consisting of a 10 mL fill in a 25 mL vial (20R). The nonclinical humanized 2A4 drug substance (200 mg/vial) is 20 mL fill in a 25 mL vial (20R). The nonclinical and clinical formulations of humanized 2A4 are provided in Table 1. The final formulation of the humanized 2A4 drug substance has a density of 1.034 g/mL at 20° C. and a pH of 6.5.

TABLE 1

Composition of Nonclinical and Clinical Humanized 2A4 Drug Substance

| Component | Function | Concentration (g/L) | Nominal amount (mg/vial) Nonclinical Vial Size = 25 mL (20R) | Clinical Vial Size = 25 mL (20R) |
|---|---|---|---|---|
| Humanized 2A4 drug substance | Active Substance | 10 | 200 | 100 |
| L-Histidine | Buffer component | 2.72 | 54.4 | 27.2 |
| L-Histidine HCl monohydrate | Buffer component | 1.57 | 31.4 | 15.7 |
| Trehalose dihydrate | Tonicity agent | 87.02 | 1,740.4 | 870.2 |
| Polysorbate (TWEEN ®) 20 | Surfactant | 0.20 | 4.0 | 2.0 |
| Water for Injection (WFI) | Solvent | — | Add WFI to a total volume of 20 mL | Add WFI to a total volume of 10 mL |

Example 9. Batch Formula for Drug Product (100 mg/ml Vial)

A formula was designed for a 2,600 vial batch of drug product as provided in Table 2.

TABLE 2

Batch Formula for 2,600 Vials

| Ingredient | Grade | Quantity per Batch |
|---|---|---|
| Humanized 2A4 antibody | — | 260.0 g |
| L-Histidine | USP, Ph. Eur. | 70.72 g |
| L-Histidine HCl monohydrate | Ph. Eur. | 40.82 g |
| Trehalose dehydrate | USP/NF, Ph. Eur. | 2,262.52 g |
| Polysorbate 20 | USP/NF, Ph. Eur. | 5.20 g |

Example 10. Lyophilization

A Hof Com 26041 freeze dryer was used to lyophilize the formulated humanized 2A4 drug substance over a period of approximately 86 hours with the pressure regulated by an MKS control system (MKS Instruments) with $N_2$ injection according to the program set forth in Table 3. The endpoint was detected by Pirani signal. During the drying mode, the vials stand directly on the shelves without lyo plates. The nitrogen backfill is at approximately 600 mbar with pharma grade, sterile $N_2$. The vials were then closed and sorted at 5° C. within the freeze dryer. The final drug product is stored at 2-8° C., protected from light. The process should yield a white to yellowish lyo cake.

Table 3 summarizes the program for the lyophilization of humanized 2A4 drug substance.

TABLE 3

Lyophilization Steps

| Step | Step No. | Time [hh:mm] | Shelf temperature [° C.] | Vacuum MKS [mbar] |
|---|---|---|---|---|
| Loading | 01 | 00:01 | 5 | off |
| Freezing | 02 | 00:15 | 5 | off |
|  | 03 | 00:05 | 2 | off |
|  | 04 | 02:00 | 2 | off |
|  | 05 | 01:05 | −50 | off |
|  | 06 | 02:30 | −50 | off |

TABLE 3-continued

Lyophilization Steps

| Step | Step No. | Time [hh:mm] | Shelf temperature [° C.] | Vacuum MKS [mbar] |
|---|---|---|---|---|
| Primary Drying | 07 | 00:05 | −50 | 0.10 |
|  | 08 | 00:40 | −10 | 0.10 |
|  | 09 | 55:00 | −10 | 0.10 |
| Secondary Drying | 10 | 04:30 | 30 | 0.10 |
|  | 11 | 20:00 | 30 | 0.10 |
| Total Time |  | 86:11 |  |  |

Example 11. Reconstitution of Lyophilized Drug Product

Prior to application, the lyophlisate has to be reconstituted with sterilized water for injection. The reconstitution of h2A4 vials has been performed according to the following procedure under laminar air-flow. The complete flip-off-cap of the respective product vial was removed. The rubber-stopper was also removed. The solvent was added by pipetting the necessary volume (2×5 mL WFI using a piston pipette). When performing this action, it was ensured that the solvent was added slowly to the lyophilized product. The vials were carefully swirled (not shaken), until the lyophilized product was completely dissolved. The solution was made homogenous by carefully rotating the vial end-over-end. The dissolved material was aliquoted according to table 1 and stored at −70° C. until analysis Example 12. Clinical Assessment of Humanized 2A4 Drug Substance A clinical trial is designed to determine a maximum tolerated dose (MTD) and/or the Phase 2 recommended dose (P2RD) of humanized 2A4 drug substance in subjects with AL amyloidosis. Dosing will begin at 0.5 mg/kg and escalate to a high of 30 mg/kg or 2500 mg total (whichever is lower). Initially, humanized 2A4 drug substance will be given intravenously as a single agent every 28 days until progression of organ function or unacceptable treatment related toxicity or withdraw of consent. If the half-life ($t_{1/2}$) of humanized 2A4 drug substance from the initial doses suggests that a different dosing schedule would be more appropriate (e.g., every two weeks or an alternate, less frequent schedule than once every 28 days), dosing in subsequent cohorts may be modified using an alternative dosing schedule.

What is claimed is:

1. A method of therapeutically treating a human patient having AL amyloidosis characterized by the presence of amyloid protein fibrils, the method comprising administering to the patient an effective dosage of a reconstituted lyophilized formulation of a humanized version of antibody 2A4 (ATCC Accession Number PTA-9662) or antibody 7D8 (ATCC Accession Number PTA-9468) or antigen-binding fragment thereof comprising:
   (a) the antibody at a concentration of about 10 mg/ml;
   (b) a histidine buffer at a concentration of about 25 mM;
   (c) trehalose at a concentration of about 230 mM;
   (d) polysorbate 20 at a concentration of about 0.2 g/L; and
   wherein the reconstituted formulation has a pH of about 6.5.

2. The method of claim 1, wherein the human patient is also treated with at least one second drug selected from the group consisting of melphalan, bortezomib, lenolidomide or carfilzomib.

3. The method of claim 2, wherein the at least one second drug is bortezomib.

4. The method of claim 1, wherein the AL amyloidosis is associated with a dyscrasia of the B lymphocyte lineage.

5. The method of claim 4, wherein the dyscrasia is a malignancy.

6. The method of claim 5, wherein the malignancy is multiple myeloma.

7. The method of claim 1, wherein the reconstituted formulation is administered to the human patient at a frequency in a range of about daily to about annually.

8. The method of claim 7, wherein the reconstituted formulation is administered to the human patient once every twenty-eight days.

9. The method of claim 8, wherein at least one second drug is administered to the human patient at a frequency of daily to annually.

10. The method of claim 9, wherein the at least one second drug is administered to the human patient once every seven days.

11. The method of claim 1, wherein the formulation is administered to the human patient in a dose ranging from 0.5 mg of antibody per kg body weight of the human patient to 30 mg of antibody per kg of body weight of the patient.

12. The method of claim 11, wherein the formulation is administered to the human patient in a dose ranging from 20 mg of antibody per kg body weight of the human patient to 30 mg of antibody per kg of body weight of the patient.

13. The method of claim 12, wherein the formulation is administered to the human patient in a dose of 25 mg of antibody per kg body weight of the human patient.

14. The method of claim 1, wherein the formulation is administered to the human patient in a dose ranging from 10 mg of the antibody to 5000 mg of the antibody.

15. The method of claim 14, wherein the formulation is administered to the human patient in a dose ranging from 30 mg of the antibody to 2500 mg of the antibody.

16. The method of claim 1, wherein the antibody comprises a light chain variable region comprising an amino acid sequence set forth as SEQ ID NO: 4 and a heavy chain variable region comprising an amino acid sequence set forth as SEQ ID NO: 5.

17. The method of claim 1, wherein the antibody comprises a light chain comprising an amino acid sequence set forth as SEQ ID NO: 13 and a heavy chain comprising an amino acid sequence set forth as SEQ ID NO: 15.

18. A method of therapeutically treating a human patient having AL amyloidosis characterized by the presence of amyloid protein fibrils, the method comprising administering to the patient an effective dosage of a reconstituted lyophilized formulation comprising:
   (a) an antibody comprising a light chain comprising an amino acid sequence set forth as SEQ ID NO: 13 and a heavy chain comprising an amino acid sequence set forth as any one of SEQ ID NOs: 14-16, and which is present at a concentration of 50 mg/mL;
   (b) a histidine buffer present at a concentration of 25 mM;
   (c) trehalose present at a concentration of 230 mM;
   (d) polysorbate 20 present at a concentration of 0.2 g/L; and
   wherein the reconstituted formulation has a pH of 6.5.

19. The method of claim 18, wherein the reconstituted lyophilized formulation is administered to the human patient in a dose comprising 25 mg of antibody per kg body weight of the human patient.

20. The method of claim 19, wherein the reconstituted lyophilized formulation is administered to the human patient once every 28 days.

21. The method of claim 20, wherein the reconstituted lyophilized formulation is administered to the human patient with bortezomib.

22. The method of claim 21, wherein the bortezomib is administered to the human patient every seven days.

23. A method of therapeutically treating a human patient having AL amyloidosis characterized by the presence of amyloid protein fibrils, the method comprising administering to the patient an effective dosage of a reconstituted lyophilized formulation comprising:
  (a) an antibody comprising a light chain comprising an amino acid sequence set forth as SEQ ID NO: 13 and a heavy chain comprising an amino acid sequence set forth as any one of SEQ ID NOs: 14-16, and which is present at a concentration of 50 mg/mL;
  (b) a histidine buffer present at a concentration of 25 mM;
  (c) trehalose present at a concentration of 230 mM;
  (d) polysorbate 20 present at a concentration of 0.2 g/L;
  wherein the reconstituted formulation has a pH of 6.5; and
  wherein the reconstituted lyophilized formulation is administered to the human patient in a dose comprising 25 mg of antibody per kg body weight of the human patient once every 28 days and bortezomib is administered to the human patient every seven days.

* * * * *

SEQUENCE LISTING

```
<160> NUMBER OF SEQ ID NOS: 24

<210> SEQ ID NO 1
<211> LENGTH: 131
<212> TYPE: PRT
<213> ORGANISM: Mus musculus
<220> FEATURE:
<221> NAME/KEY: MISC_FEATURE
<222> LOCATION: (1)..(19)
<223> OTHER INFORMATION: LEADER SEQUENCE
<220> FEATURE:
<221> NAME/KEY: mat_peptide
<222> LOCATION: (20)..(131)
<220> FEATURE:
<221> NAME/KEY: MISC_FEATURE
<222> LOCATION: (43)..(58)
<223> OTHER INFORMATION: CDR 1
<220> FEATURE:
<221> NAME/KEY: MISC_FEATURE
<222> LOCATION: (74)..(80)
<223> OTHER INFORMATION: CDR 2
<220> FEATURE:
<221> NAME/KEY: MISC_FEATURE
<222> LOCATION: (113)..(121)
<223> OTHER INFORMATION: CDR 3

<400> SEQUENCE: 1

Met Lys Leu Pro Val Arg Leu Leu Val Leu Met Phe Trp Ile Pro Ala
                -15                 -10                  -5

Ser Ser Ser Asp Val Val Met Thr Gln Thr Pro Leu Ser Leu Pro Val
         -1   1               5                       10

Ser Leu Gly Asp Gln Ala Ser Ile Ser Cys Arg Ser Ser Gln Ser Leu
     15                  20                  25

Val His Ser Thr Gly Asn Thr Tyr Leu His Trp Tyr Leu Gln Lys Pro
 30                  35                  40                  45

Gly Gln Ser Pro Lys Leu Leu Ile Tyr Lys Val Ser Asn Arg Phe Ser
                 50                  55                  60

Gly Val Pro Asp Arg Phe Ser Gly Ser Gly Ser Gly Thr Tyr Phe Thr
                 65                  70                  75

Leu Lys Ile Ser Arg Val Glu Ala Glu Asp Leu Gly Val Tyr Phe Cys
             80                  85                  90

Ser Gln Ser Thr His Val Pro Phe Thr Phe Gly Gly Gly Thr Lys Leu
     95                 100                 105

Glu Ile Lys
110

<210> SEQ ID NO 2
<211> LENGTH: 131
<212> TYPE: PRT
<213> ORGANISM: Mus musculus
<220> FEATURE:
<221> NAME/KEY: MISC_FEATURE
<222> LOCATION: (1)..(19)
<223> OTHER INFORMATION: LEADER SEQUENCE
<220> FEATURE:
<221> NAME/KEY: mat_peptide
```

```
<222> LOCATION: (20)..(131)
<220> FEATURE:
<221> NAME/KEY: MISC_FEATURE
<222> LOCATION: (43)..(58)
<223> OTHER INFORMATION: CDR1
<220> FEATURE:
<221> NAME/KEY: MISC_FEATURE
<222> LOCATION: (74)..(80)
<223> OTHER INFORMATION: CDR2
<220> FEATURE:
<221> NAME/KEY: MISC_FEATURE
<222> LOCATION: (113)..(121)
<223> OTHER INFORMATION: CDR3

<400> SEQUENCE: 2

Met Lys Leu Pro Val Arg Leu Leu Val Leu Met Phe Trp Ile Pro Ala
            -15                 -10                 -5

Ser Ser Ser Asp Val Val Met Thr Gln Thr Pro Leu Ser Leu Pro Val
        -1   1               5                  10

Ser Leu Gly Asp Gln Ala Ser Ile Ser Cys Arg Ser Ser Leu Ser Leu
        15                  20                  25

Val His Ser Thr Gly Asn Thr Tyr Leu His Trp Tyr Leu Gln Lys Pro
 30                  35                  40                  45

Gly Gln Ser Pro Lys Leu Leu Ile Tyr Lys Val Ser Asn Arg Phe Ser
                50                  55                  60

Gly Val Pro Asp Arg Phe Ser Gly Ser Gly Ser Gly Thr Tyr Phe Thr
                65                  70                  75

Leu Lys Ile Ser Arg Val Glu Ala Glu Asp Leu Gly Val Tyr Phe Cys
        80                  85                  90

Ser Gln Ser Thr His Val Pro Phe Thr Phe Gly Gly Gly Thr Lys Leu
        95                 100                 105

Glu Ile Lys
110

<210> SEQ ID NO 3
<211> LENGTH: 138
<212> TYPE: PRT
<213> ORGANISM: Mus musculus
<220> FEATURE:
<221> NAME/KEY: MISC_FEATURE
<222> LOCATION: (1)..(19)
<223> OTHER INFORMATION: LEADER SEQUENCE
<220> FEATURE:
<221> NAME/KEY: mat_peptide
<222> LOCATION: (20)..(138)
<220> FEATURE:
<221> NAME/KEY: MISC_FEATURE
<222> LOCATION: (45)..(54)
<223> OTHER INFORMATION: CDR 1
<220> FEATURE:
<221> NAME/KEY: MISC_FEATURE
<222> LOCATION: (69)..(87)
<223> OTHER INFORMATION: CDR 2
<220> FEATURE:
<221> NAME/KEY: MISC_FEATURE
<222> LOCATION: (120)..(127)
<223> OTHER INFORMATION: CDR 3

<400> SEQUENCE: 3

Met Val Leu Gly Leu Lys Trp Val Phe Phe Val Val Phe Tyr Gln Gly
            -15                 -10                 -5

Val His Cys Glu Val Gln Leu Val Glu Ser Gly Gly Arg Leu Val Gln
        -1   1               5                  10

Pro Lys Gly Ser Leu Lys Leu Ser Cys Ala Ala Ser Gly Phe Thr Phe
        15                  20                  25
```

Asn Thr Tyr Ala Met Tyr Trp Ile Arg Gln Ala Pro Gly Lys Gly Leu
 30                  35                  40                  45

Glu Trp Val Ala Arg Ile Arg Ser Lys Ser Asn Asn Tyr Ala Ile Tyr
                 50                  55                  60

Tyr Ala Asp Ser Val Lys Asp Arg Phe Thr Ile Phe Arg Asp Asp Ser
             65                  70                  75

Gln Ser Met Leu Tyr Leu Gln Met Asn Asn Leu Lys Thr Glu Asp Thr
         80                  85                  90

Ala Met Tyr Tyr Cys Val Arg Pro Tyr Ser Asp Ser Phe Ala Tyr Trp
     95                 100                 105

Gly Gln Gly Thr Leu Val Thr Val Ser Ala
110                 115

<210> SEQ ID NO 4
<211> LENGTH: 112
<212> TYPE: PRT
<213> ORGANISM: Artificial Sequence
<220> FEATURE:
<223> OTHER INFORMATION: Humanized antibody sequence containing murine
      and human residues (humanized 2A4 light chain variable region
      version 3)

<400> SEQUENCE: 4

Asp Val Val Met Thr Gln Ser Pro Leu Ser Leu Pro Val Thr Pro Gly
1               5                  10                  15

Glu Pro Ala Ser Ile Ser Cys Arg Ser Ser Gln Ser Leu Val His Ser
             20                  25                  30

Thr Gly Asn Thr Tyr Leu His Trp Tyr Leu Gln Lys Pro Gly Gln Ser
         35                  40                  45

Pro Gln Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                 85                  90                  95

Thr His Val Pro Phe Thr Phe Gly Gly Gly Thr Lys Val Glu Ile Lys
            100                 105                 110

<210> SEQ ID NO 5
<211> LENGTH: 119
<212> TYPE: PRT
<213> ORGANISM: Artificial Sequence
<220> FEATURE:
<223> OTHER INFORMATION: Humanized antibody sequence containing murine
      and human residues (humanized 2A4 heavy chain variable region
      version 3)

<400> SEQUENCE: 5

Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Phe Asn Thr Tyr
             20                  25                  30

Ala Met Tyr Trp Ile Arg Gln Ala Pro Gly Lys Gly Leu Glu Trp Val
         35                  40                  45

Ala Arg Ile Arg Ser Lys Ser Asn Asn Tyr Ala Ile Tyr Tyr Ala Asp
     50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr

```
                    85                  90                  95
Tyr Cys Ala Arg Pro Tyr Ser Asp Ser Phe Ala Tyr Trp Gly Gln Gly
                100                 105                 110

Thr Leu Val Thr Val Ser Ser
        115

<210> SEQ ID NO 6
<211> LENGTH: 16
<212> TYPE: PRT
<213> ORGANISM: Mus musculus
<220> FEATURE:
<221> NAME/KEY: MISC_FEATURE
<222> LOCATION: (1)..(16)
<223> OTHER INFORMATION: 2A4 VL CDR1

<400> SEQUENCE: 6

Arg Ser Ser Gln Ser Leu Val His Ser Thr Gly Asn Thr Tyr Leu His
1               5                   10                  15

<210> SEQ ID NO 7
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: 2A4 VL CDR2

<400> SEQUENCE: 7

Lys Val Ser Asn Arg Phe Ser
1               5

<210> SEQ ID NO 8
<211> LENGTH: 9
<212> TYPE: PRT
<213> ORGANISM: Mus musculus
<220> FEATURE:
<221> NAME/KEY: MISC_FEATURE
<222> LOCATION: (1)..(9)
<223> OTHER INFORMATION: 2A4 VL CDR3

<400> SEQUENCE: 8

Ser Gln Ser Thr His Val Pro Phe Thr
1               5

<210> SEQ ID NO 9
<211> LENGTH: 10
<212> TYPE: PRT
<213> ORGANISM: Mus musculus
<220> FEATURE:
<221> NAME/KEY: MISC_FEATURE
<222> LOCATION: (1)..(10)
<223> OTHER INFORMATION: 2A4 VH CDR1

<400> SEQUENCE: 9

Gly Phe Thr Phe Asn Thr Tyr Ala Met Tyr
1               5                   10

<210> SEQ ID NO 10
<211> LENGTH: 19
<212> TYPE: PRT
<213> ORGANISM: Mus musculus
<220> FEATURE:
<221> NAME/KEY: MISC_FEATURE
<222> LOCATION: (1)..(19)
<223> OTHER INFORMATION: 2A4 VH CDR2

<400> SEQUENCE: 10
```

```
Arg Ile Arg Ser Lys Ser Asn Asn Tyr Ala Ile Tyr Tyr Ala Asp Ser
1               5                   10                  15

Val Lys Asp

<210> SEQ ID NO 11
<211> LENGTH: 8
<212> TYPE: PRT
<213> ORGANISM: Mus musculus
<220> FEATURE:
<221> NAME/KEY: MISC_FEATURE
<222> LOCATION: (1)..(8)
<223> OTHER INFORMATION: 2A4 VH CDR3

<400> SEQUENCE: 11

Pro Tyr Ser Asp Ser Phe Ala Tyr
1               5

<210> SEQ ID NO 12
<211> LENGTH: 16
<212> TYPE: PRT
<213> ORGANISM: Mus musculus
<220> FEATURE:
<221> NAME/KEY: MISC_FEATURE
<222> LOCATION: (1)..(16)
<223> OTHER INFORMATION: 7D8 VL CDR1

<400> SEQUENCE: 12

Arg Ser Ser Leu Ser Leu Val His Ser Thr Gly Asn Thr Tyr Leu His
1               5                   10                  15

<210> SEQ ID NO 13
<211> LENGTH: 219
<212> TYPE: PRT
<213> ORGANISM: Artificial Sequence
<220> FEATURE:
<223> OTHER INFORMATION: Humanized antibody sequence containing murine
      and human residues (humanized 2A4 kappa light chain)

<400> SEQUENCE: 13

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
                20                  25                  30

Thr Gly Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Phe Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
```

```
                     165                 170                 175
Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 14
<211> LENGTH: 449
<212> TYPE: PRT
<213> ORGANISM: Artificial Sequence
<220> FEATURE:
<223> OTHER INFORMATION: Humanized antibody sequence containing murine
      and human residues (humanized 2A4 IgG1 heavy chain variant 1
      (G1m1 allotype))

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Tyr Trp Ile Arg Gln Ala Pro Gly Lys Gly Leu Glu Trp Val
        35                  40                  45

Ala Arg Ile Arg Ser Lys Ser Asn Asn Tyr Ala Ile Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Pro Tyr Ser Asp Ser Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300
```

```
Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys

<210> SEQ ID NO 15
<211> LENGTH: 449
<212> TYPE: PRT
<213> ORGANISM: Artificial Sequence
<220> FEATURE:
<223> OTHER INFORMATION: Humanized antibody sequence containing murine
      and human residues (humanized 2A4 IgG1 heavy chain variant 2
      (G1m3 allotype))
<220> FEATURE:
<221> NAME/KEY: MISC_FEATURE
<222> LOCATION: (299)..(301)
<223> OTHER INFORMATION: glycosylation site

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Tyr Trp Ile Arg Gln Ala Pro Gly Lys Gly Leu Glu Trp Val
        35                  40                  45

Ala Arg Ile Arg Ser Lys Ser Asn Asn Tyr Ala Ile Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Pro Tyr Ser Asp Ser Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

```
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
            195                 200                 205
Ser Asn Thr Lys Val Asp Lys Arg Val Glu Pro Lys Ser Cys Asp Lys
            210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
            245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
            275                 280                 285
Ala Lys Thr Lys Pro Arg Glu Glu Gln Tyr Asn Ser Thr Tyr Arg Val
            290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
            325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
            355                 360                 365
Cys Leu Val Lys Gly Phe Tyr Pro Ser Asp Ile Ala Val Glu Trp Glu
            370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
            405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
            435                 440                 445
Lys

<210> SEQ ID NO 16
<211> LENGTH: 445
<212> TYPE: PRT
<213> ORGANISM: Artificial Sequence
<220> FEATURE:
<223> OTHER INFORMATION: Humanized antibody sequence containing murine
      and human residues (humanized 2A4 IgG2 heavy chain)

<400> SEQUENCE: 16

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Asn Thr Tyr
            20                  25                  30
Ala Met Tyr Trp Ile Arg Gln Ala Pro Gly Lys Gly Leu Glu Trp Val
            35                  40                  45
Ala Arg Ile Arg Ser Lys Ser Asn Asn Tyr Ala Ile Tyr Tyr Ala Asp
            50                  55                  60
Ser Val Lys Asp Arg Phe Thr Ile Ser Arg Asp Asp Ser Lys Asn Ser
65                  70                  75                  80
```

-continued

```
Leu Tyr Leu Gln Met Asn Ser Leu Lys Thr Glu Asp Thr Ala Val Tyr
                 85                  90                  95
Tyr Cys Ala Arg Pro Tyr Ser Asp Ser Phe Ala Tyr Trp Gly Gln Gly
            100                 105                 110
Thr Leu Val Thr Val Ser Ser Ala Ser Thr Lys Gly Pro Ser Val Phe
        115                 120                 125
Pro Leu Ala Pro Cys Ser Arg Ser Thr Ser Glu Ser Thr Ala Ala Leu
130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Asn Phe Gly Thr Gln Thr Tyr Thr Cys Asn Val Asp His Lys Pro
        195                 200                 205
Ser Asn Thr Lys Val Asp Lys Thr Val Glu Arg Lys Cys Cys Val Glu
    210                 215                 220
Cys Pro Pro Cys Pro Ala Pro Pro Val Ala Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Gln
            260                 265                 270
Phe Asn Trp Tyr Val Asp Gly Val Glu Val His Asn Ala Lys Thr Lys
        275                 280                 285
Pro Arg Glu Glu Gln Phe Asn Ser Thr Phe Arg Val Val Ser Val Leu
    290                 295                 300
Thr Val Val His Gln Asp Trp Leu Asn Gly Lys Glu Tyr Lys Cys Lys
305                 310                 315                 320
Val Ser Asn Lys Gly Leu Pro Ala Pro Ile Glu Lys Thr Ile Ser Lys
                325                 330                 335
Thr Lys Gly Gln Pro Arg Glu Pro Gln Val Tyr Thr Leu Pro Pro Ser
            340                 345                 350
Arg Glu Glu Met Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
    370                 375                 380
Pro Glu Asn Asn Tyr Lys Thr Thr Pro Pro Met Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
His Tyr Thr Gln Lys Ser Leu Ser Leu Ser Pro Gly Lys
        435                 440                 445

<210> SEQ ID NO 17
<211> LENGTH: 7
<212> TYPE: PRT
<213> ORGANISM: Homo sapiens

<400> SEQUENCE: 17

Cys Gly Gly His Glu Asp Thr
1               5
```

<210> SEQ ID NO 18
<211> LENGTH: 4
<212> TYPE: PRT
<213> ORGANISM: Homo sapiens

<400> SEQUENCE: 18

Ala Glu Asp Ser
1

<210> SEQ ID NO 19
<211> LENGTH: 660
<212> TYPE: DNA
<213> ORGANISM: Artificial Sequence
<220> FEATURE:
<223> OTHER INFORMATION: Humanized antibody sequence containing murine
      and human residues (Hu2A4 VH3VL3 hcg1,k cDNA sequence - light
      chain without signal
      sequence)

<400> SEQUENCE: 19
gacgtggtga tgacccagtc ccctctgtcc ctgcctgtga cccctggcga gcctgcctcc      60
atctcctgcc ggtcctccca gtccctggtg cactccaccg gcaacaccta tctgcactgg     120
tatctgcaga gcctggcca gtctcctcag ctgctgatct acaaggtgtc caaccggttc     180
tccggcgtgc ctgaccggtt ctctggctcc ggctccggca ccgacttcac cctgaagatc     240
tcccgggtgg aggccgagga cgtgggcgtg tactactgct cccagtccac ccacgtgcct     300
ttcaccttcg gcggaggcac caaggtggag atcaagcgaa ctgtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctc     540
agcagcaccc tgacgctgag caaagcagac tacgagaaac acaaagtcta cgcctgcgaa     600
gtcacccatc agggcctgag ctcgcccgtc acaaagagct tcaacagggg agagtgttag     660

<210> SEQ ID NO 20
<211> LENGTH: 726
<212> TYPE: DNA
<213> ORGANISM: Artificial Sequence
<220> FEATURE:
<223> OTHER INFORMATION: Humanized antibody sequence containing murine
      and human residues (Hu2A4 VH3VL3 hcg1,k cDNA sequence - light
      chain)
<220> FEATURE:
<221> NAME/KEY: sig_peptide
<222> LOCATION: (1)..(66)
<220> FEATURE:
<221> NAME/KEY: CDS
<222> LOCATION: (1)..(726)
<220> FEATURE:
<221> NAME/KEY: V_region
<222> LOCATION: (67)..(402)
<220> FEATURE:
<221> NAME/KEY: C_region
<222> LOCATION: (403)..(726)

<400> SEQUENCE: 20 atg gac atg cgg gtg ccc gca cag ctg ctg ggc ctg ctg atg ctg tgg      48
Met Asp Met Arg Val Pro Ala Gln Leu Leu Gly Leu Leu Met Leu Trp
1               5                   10                  15 gtg tcc ggc tcc tcc ggc gac gtg gtg atg acc cag tcc cct ctg tcc      96
Val Ser Gly Ser Ser Gly Asp Val Val Met Thr Gln Ser Pro Leu Ser
            20                  25                  30

```
ctg cct gtg acc cct ggc gag cct gcc tcc atc tcc tgc cgg tcc tcc      144
Leu Pro Val Thr Pro Gly Glu Pro Ala Ser Ile Ser Cys Arg Ser Ser
         35                  40                  45 cag tcc ctg gtg cac tcc acc ggc aac acc tat ctg cac tgg tat ctg      192
Gln Ser Leu Val His Ser Thr Gly Asn Thr Tyr Leu His Trp Tyr Leu
 50                  55                  60 cag aag cct ggc cag tct cct cag ctg ctg atc tac aag gtg tcc aac      240
Gln Lys Pro Gly Gln Ser Pro Gln Leu Leu Ile Tyr Lys Val Ser Asn
65                  70                  75                  80 cgg ttc tcc ggc gtg cct gac cgg ttc tct ggc tcc ggc tcc ggc acc      288
Arg Phe Ser Gly Val Pro Asp Arg Phe Ser Gly Ser Gly Ser Gly Thr
                 85                  90                  95 gac ttc acc ctg aag atc tcc cgg gtg gag gcc gag gac gtg ggc gtg      336
Asp Phe Thr Leu Lys Ile Ser Arg Val Glu Ala Glu Asp Val Gly Val
            100                 105                 110 tac tac tgc tcc cag tcc acc cac gtg cct ttc acc ttc ggc gga ggc      384
Tyr Tyr Cys Ser Gln Ser Thr His Val Pro Phe Thr Phe Gly Gly Gly
        115                 120                 125 acc aag gtg gag atc aag cga act gtg gct gca cca tct gtc ttc atc      432
Thr Lys Val Glu Ile Lys Arg Thr Val Ala Ala Pro Ser Val Phe Ile
    130                 135                 140 ttc ccg cca tct gat gag cag ttg aaa tct gga act gcc tct gtt gtg      480
Phe Pro Pro Ser Asp Glu Gln Leu Lys Ser Gly Thr Ala Ser Val Val
145                 150                 155                 160 tgc ctg ctg aat aac ttc tat ccc aga gag gcc aaa gta cag tgg aag      528
Cys Leu Leu Asn Asn Phe Tyr Pro Arg Glu Ala Lys Val Gln Trp Lys
                165                 170                 175 gtg gat aac gcc ctc caa tcg ggt aac tcc cag gag agt gtc aca gag      576
Val Asp Asn Ala Leu Gln Ser Gly Asn Ser Gln Glu Ser Val Thr Glu
            180                 185                 190 cag gac agc aag gac agc acc tac agc ctc agc agc acc ctg acg ctg      624
Gln Asp Ser Lys Asp Ser Thr Tyr Ser Leu Ser Ser Thr Leu Thr Leu
        195                 200                 205 agc aaa gca gac tac gag aaa cac aaa gtc tac gcc tgc gaa gtc acc      672
Ser Lys Ala Asp Tyr Glu Lys His Lys Val Tyr Ala Cys Glu Val Thr
    210                 215                 220 cat cag ggc ctg agc tcg ccc gtc aca aag agc ttc aac agg gga gag      720
His Gln Gly Leu Ser Ser Pro Val Thr Lys Ser Phe Asn Arg Gly Glu
225                 230                 235                 240 tgt tag                                                               726
Cys

<210> SEQ ID NO 21
<211> LENGTH: 241
<212> TYPE: PRT
<213> ORGANISM: Artificial Sequence
<220> FEATURE:
<223> OTHER INFORMATION: Synthetic Construct

<400> SEQUENCE: 21

Met Asp Met Arg Val Pro Ala Gln Leu Leu Gly Leu Leu Met Leu Trp
 1               5                  10                  15

Val Ser Gly Ser Ser Gly Asp Val Val Met Thr Gln Ser Pro Leu Ser
             20                  25                  30

Leu Pro Val Thr Pro Gly Glu Pro Ala Ser Ile Ser Cys Arg Ser Ser
         35                  40                  45

Gln Ser Leu Val His Ser Thr Gly Asn Thr Tyr Leu His Trp Tyr Leu
     50                  55                  60

Gln Lys Pro Gly Gln Ser Pro Gln Leu Leu Ile Tyr Lys Val Ser Asn
65                  70                  75                  80
```

```
Arg Phe Ser Gly Val Pro Asp Arg Phe Ser Gly Ser Gly Thr
                85                  90                  95
Asp Phe Thr Leu Lys Ile Ser Arg Val Glu Ala Glu Asp Val Gly Val
                100                 105                 110
Tyr Tyr Cys Ser Gln Ser Thr His Val Pro Phe Thr Phe Gly Gly Gly
            115                 120                 125
Thr Lys Val Glu Ile Lys Arg Thr Val Ala Ala Pro Ser Val Phe Ile
130                 135                 140
Phe Pro Pro Ser Asp Glu Gln Leu Lys Ser Gly Thr Ala Ser Val Val
145                 150                 155                 160
Cys Leu Leu Asn Asn Phe Tyr Pro Arg Glu Ala Lys Val Gln Trp Lys
                165                 170                 175
Val Asp Asn Ala Leu Gln Ser Gly Asn Ser Gln Glu Ser Val Thr Glu
            180                 185                 190
Gln Asp Ser Lys Asp Ser Thr Tyr Ser Leu Ser Ser Thr Leu Thr Leu
        195                 200                 205
Ser Lys Ala Asp Tyr Glu Lys His Lys Val Tyr Ala Cys Glu Val Thr
210                 215                 220
His Gln Gly Leu Ser Ser Pro Val Thr Lys Ser Phe Asn Arg Gly Glu
225                 230                 235                 240
Cys

<210> SEQ ID NO 22
<211> LENGTH: 1350
<212> TYPE: DNA
<213> ORGANISM: Artificial Sequence
<220> FEATURE:
<223> OTHER INFORMATION: Humanized antibody sequence containing murine
      and human residues (Hu2A4 VH3VL3 hcg1,k cDNA sequence - heavy
      chain without signal
      sequence)

<400> SEQUENCE: 22
gaggtgcagc tggtcgagtc cggcggaggc ctggtgcagc ctggcggctc cctgagactg      60
tcctgcgccg cctccggctt caccttcaac acctacgcca tgtactggat caggcaggct    120
cctggcaagg gactggagtg ggtggcccgg atcaggtcca agtccaacaa ctacgctatc    180
tactacgccg actccgtgaa ggaccggttc accatctccc gggacgactc caagaactcc    240
ctgtatctgc agatgaactc cctgaaaacc gaggacaccg ccgtgtacta ctgcgctcgg    300
ccttactccg actccttcgc ctactggggc agggcacccc tggtgaccgt gtccagcgcc    360
tccaccaagg gcccatcggt cttccccctg gcaccctcct ccaagagcac ctctggggcc    420
acagcggccc tgggctgcct ggtcaaggac tacttccccg aaccggtgac ggtgtcgtgg    480
aactcaggcg ccctgaccag cggcgtgcac accttcccgg ctgtcctaca gtcctcagga    540
ctctactccc tcagcagcgt ggtgaccgtg ccctccagca gcttgggcac ccagacctac    600
atctgcaacg tgaatcacaa gcccagcaac accaaggtgg acaagagagt tgagcccaaa    660
tcttgtgaca aaactcacac atgcccaccg tgcccagcac ctgaactcct ggggggaccg    720
tcagtcttcc tcttccccc aaaacccaag gacaccctca tgatctcccg gacccctgag    780
gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccgtg tggtcagcgt cctcaccgtc ctgcaccagg actggctgaa tggcaaggag    960
tacaagtgca aggtctccaa caaagccctc ccagccccca tcgagaaaac catctccaaa   1020
```

-continued

```
gccaaagggc agccccgaga accacaggtg tacacgctgc ccccatcccg ggaggagatg    1080
accaagaacc aggtcagcct gacctgcctg gtcaaaggct tctatcccag cgacatcgcc    1140
gtggagtggg agagcaatgg gcagccggag aacaactaca agaccacgcc tcccgtgctg    1200
gactccgacg gctccttctt cctctatagc aagctcaccg tggacaagag caggtggcag    1260
caggggaacg tcttctcatg ctccgtgatg catgaggctc tgcacaacca ctacacgcag    1320
aagagcctct ccctgtcccc gggtaaatga                                     1350
```

```
<210> SEQ ID NO 23
<211> LENGTH: 1407
<212> TYPE: DNA
<213> ORGANISM: Artificial Sequence
<220> FEATURE:
<223> OTHER INFORMATION: Humanized antibody sequence containing murine
      and human residues (Hu2A4 VH3VL3 hcg1,k cDNA sequence - heavy
      chain)
<220> FEATURE:
<221> NAME/KEY: sig_peptide
<222> LOCATION: (1)..(57)
<220> FEATURE:
<221> NAME/KEY: CDS
<222> LOCATION: (1)..(1407)
<220> FEATURE:
<221> NAME/KEY: V_region
<222> LOCATION: (58)..(414)
<220> FEATURE:
<221> NAME/KEY: C_region
<222> LOCATION: (415)..(1407)
```

<400> SEQUENCE: 23

```
atg gag ttc ggc ctg tcc tgg ctg ttc ctg gtg gcc atc ctg aag ggc       48
Met Glu Phe Gly Leu Ser Trp Leu Phe Leu Val Ala Ile Leu Lys Gly
1               5                   10                  15 gtg cag tgc gag gtg cag ctg gtc gag tcc gga ggc ctg gtg cag           96
Val Gln Cys Glu Val Gln Leu Val Glu Ser Gly Gly Gly Leu Val Gln
            20                  25                  30 cct ggc ggc tcc ctg aga ctg tcc tgc gcc gcc tcc ggc ttc acc ttc      144
Pro Gly Gly Ser Leu Arg Leu Ser Cys Ala Ala Ser Gly Phe Thr Phe
        35                  40                  45 aac acc tac gcc atg tac tgg atc agg cag gct cct ggc aag gga ctg      192
Asn Thr Tyr Ala Met Tyr Trp Ile Arg Gln Ala Pro Gly Lys Gly Leu
    50                  55                  60 gag tgg gtg gcc cgg atc agg tcc aag tcc aac aac tac gct atc tac      240
Glu Trp Val Ala Arg Ile Arg Ser Lys Ser Asn Asn Tyr Ala Ile Tyr
65                  70                  75                  80 tac gcc gac tcc gtg aag gac cgg ttc acc atc tcc cgg gac gac tcc      288
Tyr Ala Asp Ser Val Lys Asp Arg Phe Thr Ile Ser Arg Asp Asp Ser
                85                  90                  95 aag aac tcc ctg tat ctg cag atg aac tcc ctg aaa acc gag gac acc      336
Lys Asn Ser Leu Tyr Leu Gln Met Asn Ser Leu Lys Thr Glu Asp Thr
            100                 105                 110 gcc gtg tac tac tgc gct cgg cct tac tcc gac tcc ttc gcc tac tgg      384
Ala Val Tyr Tyr Cys Ala Arg Pro Tyr Ser Asp Ser Phe Ala Tyr Trp
        115                 120                 125 ggc cag ggc acc ctg gtg acc gtg tcc agc gcc tcc acc aag ggc cca      432
Gly Gln Gly Thr Leu Val Thr Val Ser Ser Ala Ser Thr Lys Gly Pro
    130                 135                 140 tcg gtc ttc ccc ctg gca ccc tcc tcc aag agc acc tct ggg ggc aca      480
Ser Val Phe Pro Leu Ala Pro Ser Ser Lys Ser Thr Ser Gly Gly Thr
145                 150                 155                 160 gcg gcc ctg ggc tgc ctg gtc aag gac tac ttc ccc gaa ccg gtg acg      528
Ala Ala Leu Gly Cys Leu Val Lys Asp Tyr Phe Pro Glu Pro Val Thr
```

```
                      165                 170                 175
gtg tcg tgg aac tca ggc gcc ctg acc agc ggc gtg cac acc ttc ccg      576
Val Ser Trp Asn Ser Gly Ala Leu Thr Ser Gly Val His Thr Phe Pro
            180                 185                 190 gct gtc cta cag tcc tca gga ctc tac tcc ctc agc agc gtg gtg acc      624
Ala Val Leu Gln Ser Ser Gly Leu Tyr Ser Leu Ser Ser Val Val Thr
        195                 200                 205 gtg ccc tcc agc agc ttg ggc acc cag acc tac atc tgc aac gtg aat      672
Val Pro Ser Ser Ser Leu Gly Thr Gln Thr Tyr Ile Cys Asn Val Asn
    210                 215                 220 cac aag ccc agc aac acc aag gtg gac aag aga gtt gag ccc aaa tct      720
His Lys Pro Ser Asn Thr Lys Val Asp Lys Arg Val Glu Pro Lys Ser
225                 230                 235                 240 tgt gac aaa act cac aca tgc cca ccg tgc cca gca cct gaa ctc ctg      768
Cys Asp Lys Thr His Thr Cys Pro Pro Cys Pro Ala Pro Glu Leu Leu
                245                 250                 255 ggg gga ccg tca gtc ttc ctc ttc ccc cca aaa ccc aag gac acc ctc      816
Gly Gly Pro Ser Val Phe Leu Phe Pro Pro Lys Pro Lys Asp Thr Leu
            260                 265                 270 atg atc tcc cgg acc cct gag gtc aca tgc gtg gtg gtg gac gtg agc      864
Met Ile Ser Arg Thr Pro Glu Val Thr Cys Val Val Val Asp Val Ser
        275                 280                 285 cac gaa gac cct gag gtc aag ttc aac tgg tac gtg gac ggc gtg gag      912
His Glu Asp Pro Glu Val Lys Phe Asn Trp Tyr Val Asp Gly Val Glu
    290                 295                 300 gtg cat aat gcc aag aca aag ccg cgg gag gag cag tac aac agc acg      960
Val His Asn Ala Lys Thr Lys Pro Arg Glu Glu Gln Tyr Asn Ser Thr
305                 310                 315                 320 tac cgt gtg gtc agc gtc ctc acc gtc ctg cac cag gac tgg ctg aat     1008
Tyr Arg Val Val Ser Val Leu Thr Val Leu His Gln Asp Trp Leu Asn
                325                 330                 335 ggc aag gag tac aag tgc aag gtc tcc aac aaa gcc ctc cca gcc ccc     1056
Gly Lys Glu Tyr Lys Cys Lys Val Ser Asn Lys Ala Leu Pro Ala Pro
            340                 345                 350 atc gag aaa acc atc tcc aaa gcc aaa ggg cag ccc cga gaa cca cag     1104
Ile Glu Lys Thr Ile Ser Lys Ala Lys Gly Gln Pro Arg Glu Pro Gln
        355                 360                 365 gtg tac acg ctg ccc cca tcc cgg gag gag atg acc aag aac cag gtc     1152
Val Tyr Thr Leu Pro Pro Ser Arg Glu Glu Met Thr Lys Asn Gln Val
    370                 375                 380 agc ctg acc tgc ctg gtc aaa ggc ttc tat ccc agc gac atc gcc gtg     1200
Ser Leu Thr Cys Leu Val Lys Gly Phe Tyr Pro Ser Asp Ile Ala Val
385                 390                 395                 400 gag tgg gag agc aat ggg cag ccg gag aac aac tac aag acc acg cct     1248
Glu Trp Glu Ser Asn Gly Gln Pro Glu Asn Asn Tyr Lys Thr Thr Pro
                405                 410                 415 ccc gtg ctg gac tcc gac ggc tcc ttc ttc ctc tat agc aag ctc acc     1296
Pro Val Leu Asp Ser Asp Gly Ser Phe Phe Leu Tyr Ser Lys Leu Thr
            420                 425                 430 gtg gac aag agc agg tgg cag cag ggg aac gtc ttc tca tgc tcc gtg     1344
Val Asp Lys Ser Arg Trp Gln Gln Gly Asn Val Phe Ser Cys Ser Val
        435                 440                 445 atg cat gag gct ctg cac aac cac tac acg cag aag agc ctc tcc ctg     1392
Met His Glu Ala Leu His Asn His Tyr Thr Gln Lys Ser Leu Ser Leu
    450                 455                 460 tcc ccg ggt aaa tga                                                 1407
Ser Pro Gly Lys
465
```

-continued

```
<210> SEQ ID NO 24
<211> LENGTH: 468
<212> TYPE: PRT
<213> ORGANISM: Artificial Sequence
<220> FEATURE:
<223> OTHER INFORMATION: Synthetic Construct

<400> SEQUENCE: 24

Met Glu Phe Gly Leu Ser Trp Leu Phe Leu Val Ala Ile Leu Lys Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Asn Thr Tyr Ala Met Tyr Trp Ile Arg Gln Ala Pro Gly Lys Gly Leu
    50                  55                  60

Glu Trp Val Ala Arg Ile Arg Ser Lys Ser Asn Asn Tyr Ala Ile Tyr
65                  70                  75                  80

Tyr Ala Asp Ser Val Lys Asp Arg Phe Thr Ile Ser Arg Asp Asp Ser
                85                  90                  95

Lys Asn Ser Leu Tyr Leu Gln Met Asn Ser Leu Lys Thr Glu Asp Thr
            100                 105                 110

Ala Val Tyr Tyr Cys Ala Arg Pro Tyr Ser Asp Ser Phe Ala Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Arg Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Glu Glu Met Thr Lys Asn Gln Val
```

-continued

```
            370                 375                 380
Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
                420                 425                 430

Val Asp Lys Ser Arg Trp Gln Gln Gly Asn Val Phe Ser Cys Ser Val
                435                 440                 445

Met His Glu Ala Leu His Asn His Tyr Thr Gln Lys Ser Leu Ser Leu
                450                 455                 460

Ser Pro Gly Lys
465
```